(12) United States Patent
Peng et al.

(10) Patent No.: US 7,871,826 B2
(45) Date of Patent: Jan. 18, 2011

(54) METHOD FOR DETERMINING CARBON CONTENT OF A HYDROCARBON-CONTAINING MIXTURE

(75) Inventors: Xiang-Dong Peng, Orefield, PA (US); Blaine Edward Herb, New Tripoli, PA (US); Matthew H. MacConnell, Orefield, PA (US); Winfried Stephen Hoglen, Lehighton, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 366 days.

(21) Appl. No.: 11/861,651

(22) Filed: Sep. 26, 2007

(65) Prior Publication Data

US 2009/0078912 A1 Mar. 26, 2009

(51) Int. Cl.
*G01N 33/00* (2006.01)
*G01F 1/84* (2006.01)
(52) U.S. Cl. .................. 436/139; 252/372; 73/861.356
(58) Field of Classification Search ................ 436/139; 252/372; 73/861.356
See application file for complete search history.

(56) References Cited

U.S. PATENT DOCUMENTS

| | | | |
|---|---|---|---|
| 2,757,290 A | 7/1956 | Jacobs |
| 2,763,790 A | 9/1956 | Ohmart |
| 2,898,466 A | 8/1959 | Lintz |
| 2,922,888 A | 1/1960 | Faulkner |
| 2,968,729 A | 1/1961 | Pepper |
| 3,196,271 A | 7/1965 | Wright |
| 3,421,077 A | 1/1969 | Liu |
| 3,426,593 A | 2/1969 | Jacobs |
| 3,677,067 A | 7/1972 | Miller |
| 3,715,912 A | 2/1973 | Schlatter |
| 3,903,478 A | 9/1975 | Stuart |
| 3,916,672 A | 11/1975 | Stansfeld |
| 4,277,681 A | 7/1981 | Borken |
| 4,526,480 A | 7/1985 | Ward |
| 4,535,638 A | 8/1985 | EerNisse |
| 4,574,639 A | 3/1986 | Ward |

(Continued)

FOREIGN PATENT DOCUMENTS

EP 1213566 3/2007

(Continued)

OTHER PUBLICATIONS

Topic 4: Viscosity and Fluid Flow, Mar. 8, 2007, accessed Jan. 15, 2010 online http://wps.aw.com/wps/media/objects/877/898586/topics/topic04.pdf.*

(Continued)

*Primary Examiner*—Krishnan S Menon
*Assistant Examiner*—Allison Gionta
(74) *Attorney, Agent, or Firm*—Bryan C. Hoke, Jr.

(57) ABSTRACT

A method for determining a carbon content value of a hydrocarbon-containing mixture. At least one composition-dependent bulk property of the hydrocarbon-containing mixture is measured and optionally at least one non-hydrocarbon component concentration is measured with the resulting measurements used in a carbon content correlation for calculating the carbon content of the hydrocarbon-containing mixture. The carbon content may be used in a hydrogen and/or synthesis gas production process for calculating a target flow rate of steam to be combined with the hydrocarbon-containing mixture to form a mixed feed having a target steam-to-carbon ratio.

11 Claims, 10 Drawing Sheets

U.S. PATENT DOCUMENTS

| | | |
|---|---|---|
| 4,582,991 A | 4/1986 | Leonardi-Cattolica |
| 4,644,796 A | 2/1987 | Ward |
| 4,644,803 A | 2/1987 | Ward |
| 4,677,841 A | 7/1987 | Kennedy |
| 4,835,456 A | 5/1989 | Liu |
| 5,027,076 A | 6/1991 | Horsley |
| 5,166,964 A | 11/1992 | Hasegawa |
| 5,271,267 A * | 12/1993 | Baumoel .................. 73/54.41 |
| 5,467,637 A | 11/1995 | Hasegawa |
| 6,029,501 A | 2/2000 | Nishino |
| 6,216,091 B1 | 4/2001 | Hammond |
| 6,548,814 B1 | 4/2003 | Gronli |
| 6,758,101 B2 | 7/2004 | Valentine |
| 7,010,433 B2 | 3/2006 | Morrow |

FOREIGN PATENT DOCUMENTS

| | | |
|---|---|---|
| JP | 08291195 | 5/1998 |

OTHER PUBLICATIONS

Hoglen and Valentine, Coriolis Meters Improve the Efficiency of Hydrogen Production Process, Micromotion White Paper, 2005.

Micromotion Solartron 3098 Gas Specific Gravity Transducer Technical Manual 30985020, Jun. 2006.

Micromotion Solartron Technical Specification Sheet B1253, Jan. 2007.

Shumake and Small, Mixing things up in hydrogen plants, Hydrocarbon Engineering, Nov. 2006.

* cited by examiner

METHOD FOR DETERMINING CARBON CONTENT OF A HYDROCARBON-CONTAINING MIXTURE

BACKGROUND

The present invention relates generally to hydrogen and/or synthesis gas production and more specifically to determination of the carbon content of a hydrocarbon-containing feedstock for a hydrogen and/or synthesis gas production process.

A feedstock for a hydrogen and/or synthesis gas production process, for example steam methane reforming (SMR), autothermal reforming (ATR), and catalytic partial oxidation (CPOX), is generally a hydrocarbon-containing mixture such as natural gas and may include refinery offgas. One of the properties of the hydrocarbon-containing mixture is its carbon content. The carbon content is used to determine the amount of steam to be combined with the hydrocarbon-containing mixture to form a mixed feed before introducing the mixed feed into a hydrogen-forming reactor.

The amount of steam to be combined with the hydrocarbon-containing mixture is determined by a control parameter typically called the steam-to-carbon ratio. Accurate determination of the carbon content of the hydrocarbon-containing mixture is important to the hydrogen-forming process so that a suitable amount of steam is added. An insufficient amount of steam will lead to carbon formation on the catalyst in the hydrogen-forming reactor, thereby resulting in carbon deposition and degrading the activity of the catalyst, while too much steam decreases the energy efficiency of the process.

Commonly, the carbon content is determined by analyzing the composition of the hydrocarbon-containing mixture. Typically, the composition is analyzed by mass spectroscopy or gas chromatography, which are costly and require frequent maintenance. Further, gas chromatography provides results with a time delay, so that any abrupt change in the composition is not detected until after hydrocarbon-containing mixture has already been introduced into the hydrogen-forming process.

Therefore, due to the time delay in the measurements, the steam-to-carbon ratio is often set conservatively to provide more steam than needed by the hydrogen-forming process. In this way, carbon formation on the catalyst can be avoided at the expense of the energy efficiency.

It would be desirable to provide carbon content measurements with low cost and low maintenance, preferably with little or no time delay.

To avoid the cost and maintenance of compositional analysis, attempts have been made to use approaches that do not use compositional analysis.

One approach is to assume a fixed carbon content for the hydrocarbon-containing mixture, for example when the composition varies within a small range, such as when the hydrocarbon-containing mixture is natural gas. Since underestimating the carbon content could lead to carbon formation on the catalyst, the assumed carbon content is chosen conservatively based on the historical composition of the hydrocarbon-containing mixture as determined by off-line composition analysis. Therefore the steam-to-carbon ratio is generally greater than required, resulting in a reduced energy efficiency of the hydrogen-forming process. The catalyst is also at risk if the carbon content of the hydrocarbon-containing mixture increases above its historical range.

Another approach is based on measuring density or molecular weight of the hydrocarbon-containing mixture. Sensors for measuring density or molecular weight are usually less expensive and require less maintenance than mass spectrometers and gas chromatographs.

A correlation between the carbon content of a hydrocarbon-containing mixture and density or molecular weight can be established based on the historical composition data of the hydrocarbon-containing mixture. This approach is more suitable than using a fixed carbon content for the hydrocarbon-containing mixture. A change in the carbon content due to a change in the proportion of different hydrocarbons will cause a change in the density or molecular weight, and the correlation will use this change to provide a more accurate estimate of the carbon content of the hydrocarbon-containing mixture.

FIG. 1 shows molecular weight plotted as a function of carbon number for straight chain alkanes, methane through hexane, nitrogen, carbon monoxide, carbon dioxide and hydrogen. FIG. 1 shows that there is a good linear correlation between molecular weight and the carbon number for alkanes. Hydrogen can also be included with the alkanes in the correlation. Because of the linear relationship, when these alkanes and hydrogen form a mixture, a measurement of the molecular weight is useful for determining the carbon number.

Since the accuracy of the calculated carbon number depends on the accuracy of the molecular weight, it would be desirable to provide accurate measurement of the molecular weight.

A problem with using density or molecular weight is that the density and molecular weight also depend on the non-hydrocarbon components in the hydrocarbon-containing mixture, for example nitrogen, argon, carbon dioxide, carbon monoxide and water. If the amount of these non-hydrocarbon components varies significantly, it will cause greater error in the carbon content calculated by the correlation. If the amount of non-hydrocarbon components goes outside the historical range where the correlation was developed, the correlation may become very unreliable.

It would be desirable to provide accurate carbon content values so that the steam-to-carbon ratio can be set less conservatively, thereby preventing carbon formation on the catalyst and improving energy efficiency.

The present method solves the long felt need for determining the carbon content of a hydrocarbon-containing mixture with improved accuracy and response time, thereby allowing less conservative steam-to-carbon ratios to be targeted.

Related disclosures include Japanese Patent Application No. 08-291195, U.S. Pat. No. 6,758,101 and European Pat. Application EP 1,213,566.

BRIEF SUMMARY

The present invention relates to a method for determining a carbon content value of a hydrocarbon-containing mixture.

In a first embodiment of the method for determining the carbon content value of a hydrocarbon-containing mixture, the method comprises measuring a first composition-dependent bulk property of the hydrocarbon-containing mixture to determine a first composition-dependent bulk property value; and calculating the carbon content value using at least the first composition-dependent bulk property value in a carbon content correlation. The first composition-dependent bulk property is selected from the group consisting of lower heating value, higher heating value, thermal conductivity, viscosity, molar heat capacity, specific heat capacity (i.e. mass-based heat capacity), and sonic velocity.

The method according to the first embodiment may further comprise measuring a concentration of at least one non-hydrocarbon component in the hydrocarbon-containing mixture to determine a non-hydrocarbon component concentration value wherein the step of calculating the carbon content value further uses the non-hydrocarbon component concentration value in the carbon content correlation. The at least one non-hydrocarbon component may be selected from the group consisting of nitrogen, carbon monoxide and carbon dioxide.

The method according to the first embodiment may, additionally or alternatively to measuring the concentration of at least one non-hydrocarbon component, further comprise measuring a second composition-dependent bulk property of the hydrocarbon-containing mixture to determine a second composition-dependent bulk property value wherein the step of calculating the carbon content value further uses the second composition-dependent bulk property value in the carbon content correlation.

In the first embodiment, the carbon content correlation may be a multivariable function of the first composition-dependent bulk property and the second composition-dependent bulk property.

The carbon content value may be a carbon number value. The carbon content value may be a carbon factor value.

In the first embodiment, the second composition-dependent bulk property may be selected from the group consisting of lower heating value, higher heating value, thermal conductivity, viscosity, molecular weight, density, molar heat capacity, specific heat capacity, and sonic velocity.

In the first embodiment, the carbon content correlation may be a linear function of the first composition-dependent bulk property and a linear function of the second composition-dependent bulk property.

In the first embodiment, the first composition-dependent bulk property may be higher heating value or lower heating value and the second composition-dependent bulk property may be molecular weight.

In the first embodiment, the first composition-dependent bulk property may be higher heating value or lower heating value and the second composition-dependent bulk property may be molar heat capacity.

In the first embodiment, the first composition-dependent bulk property may be higher heating value or lower heating value and the second composition-dependent bulk property may be thermal conductivity.

In the first embodiment, the first composition-dependent bulk property may be higher heating value or lower heating value and the second composition-dependent bulk property may be viscosity.

In the first embodiment, the first composition-dependent bulk property may be higher heating value or lower heating value and the second composition-dependent bulk property may be sonic velocity.

In the first embodiment, the first composition-dependent bulk property may be viscosity and the second composition-dependent bulk property may be molecular weight.

In the first embodiment, the first composition-dependent bulk property may be viscosity and the second composition-dependent bulk property may be sonic velocity.

The method for determining a carbon content value according to the first embodiment may further comprise measuring a third composition-dependent bulk property of the hydrocarbon-containing mixture to determine a third composition-dependent bulk property value, wherein the step of calculating the carbon content value further uses the third composition-dependent bulk property value.

In a second embodiment of the method for determining the carbon content value of a hydrocarbon-containing mixture, the method comprises containing a fixed mass of a reference gas in a fixed-volume enclosure, the reference gas having a reference gas temperature and a reference gas pressure; measuring a density of the hydrocarbon-containing mixture to determine a density value of the hydrocarbon-containing mixture at a first temperature and a first pressure, the first temperature equal to the reference gas temperature and the first pressure equal to the reference gas pressure; and calculating the carbon content value using the density value of the hydrocarbon-containing mixture in a carbon content correlation.

The method according to the second embodiment may further comprise measuring a concentration of at least one non-hydrocarbon component in the hydrocarbon-containing mixture to determine a non-hydrocarbon component concentration value wherein the step of calculating the carbon content value further uses the non-hydrocarbon component concentration value in the carbon content correlation. The at least one non-hydrocarbon component may be selected from the group consisting of nitrogen, carbon monoxide and carbon dioxide.

The method according to the second embodiment may, additionally or alternatively to measuring the concentration of at least one non-hydrocarbon component, further comprise measuring a second composition-dependent bulk property of the hydrocarbon-containing mixture to determine a second composition-dependent bulk property value wherein the step of calculating the carbon content value further uses the second composition-dependent bulk property value in the carbon content correlation.

In the second embodiment, the carbon content correlation may be a multivariable function of the density and the second composition-dependent bulk property.

In the second embodiment, the second composition-dependent bulk property may be selected from the group consisting of lower heating value, higher heating value, thermal conductivity, viscosity, molar heat capacity, specific heat capacity, and sonic velocity.

In the second embodiment, the carbon content correlation may be a linear function of the density and a linear function of the second composition-dependent bulk property.

In the second embodiment, the second composition-dependent bulk property may be one of higher heating value, lower heating value and viscosity.

In the second embodiment, the method for determining a carbon content value may further comprise measuring a third composition-dependent bulk property of the hydrocarbon-containing mixture to determine a third composition-dependent bulk property value, wherein the step of calculating the carbon content value further uses the third composition-dependent bulk property value.

The present invention also relates to a method for producing a mixed feed for hydrogen or synthesis gas production using the first embodiment of the method for determining the carbon content value of a hydrocarbon-containing mixture and/or using the second embodiment of the method for determining the carbon content value of a hydrocarbon-containing mixture.

In a first embodiment of the method for producing mixed feed, the method for producing mixed feed comprises measuring a first flow rate of a hydrocarbon-containing mixture thereby obtaining a measured flow rate value; measuring a first bulk property of the hydrocarbon-containing mixture to determine a first bulk property value, the first composition-dependent bulk property selected from the group consisting of lower heating value, higher heating value, thermal conductivity, viscosity, molar heat capacity, specific heat capacity and sonic velocity; calculating a carbon content value using at least the first bulk property value in a carbon content correlation; selecting a desired steam-to-carbon ratio of the mixed feed; calculating a target flow rate of a steam-containing feed required to obtain the desired steam-to-carbon ratio of the mixed feed using the measured flow rate value and the carbon content value, the steam-containing feed having a steam-containing feed flow rate; regulating the steam-containing feed flow rate so that the steam-containing feed flow rate comes closer to or equal to the target flow rate, thereby obtaining a regulated flow rate; and combining the hydrocarbon-containing mixture at the first flow rate with the steam-containing feed at the regulated flow rate to form the mixed feed.

In the first embodiment of the method for producing mixed feed, the method for producing mixed feed may further comprise measuring a concentration of at least one non-hydrocarbon component in the hydrocarbon-containing mixture to determine a non-hydrocarbon component concentration value and wherein the step of calculating the carbon content value further uses the non-hydrocarbon component concentration value in the carbon content correlation.

In the first embodiment of the method for producing mixed feed, the method for producing mixed feed may additionally or alternatively further comprise measuring a second bulk property of the hydrocarbon-containing mixture to determine a second bulk property value and wherein the step of calculating a carbon content value further uses the second bulk property value in the carbon content correlation.

The first embodiment of the method for producing mixed feed may include any of the specific features disclosed for the first embodiment of the method for determining a carbon content value of a hydrocarbon-containing mixture.

In a second embodiment of the method for producing mixed feed, the method for producing mixed feed comprises measuring a first flow rate of a hydrocarbon-containing mixture thereby obtaining a measured flow rate value; containing a fixed mass of a reference gas in a fixed-volume enclosure, the reference gas having a reference gas temperature and a reference gas pressure; measuring a density of the hydrocarbon-containing mixture to determine a density value of the hydrocarbon-containing mixture at a first temperature and a first pressure, the first temperature equal to the reference gas temperature and the first pressure equal to the reference gas pressure; calculating a carbon content value using at least the density value in a carbon content correlation; selecting a desired steam-to-carbon ratio of the mixed feed; calculating a target flow rate of a steam-containing feed required to obtain the desired steam-to-carbon ratio of the mixed feed using the measured flow rate value and the carbon content value, the steam-containing feed having a steam-containing feed flow rate; regulating the steam-containing feed flow rate so that the steam-containing feed flow rate comes closer to or equal to the target flow rate, thereby obtaining a regulated flow rate; and combining the hydrocarbon-containing mixture at the first flow rate with the steam-containing feed at the regulated flow rate to form the mixed feed.

In the second embodiment of the method for producing mixed feed, the method for producing mixed feed may further comprise measuring a concentration of at least one non-hydrocarbon component in the hydrocarbon-containing mixture to determine a non-hydrocarbon component concentration value and wherein the step of calculating the carbon content value further uses the non-hydrocarbon component concentration value in the carbon content correlation.

In the second embodiment of the method for producing mixed feed, the method for producing mixed feed may additionally or alternatively further comprise measuring a first bulk property of the hydrocarbon-containing mixture to determine a first bulk property value and wherein the step of calculating a carbon content value further uses the first bulk property value in the carbon content correlation.

The second embodiment of the method for producing mixed feed may include any of the specific features disclosed for the second embodiment of the method for determining a carbon content value of a hydrocarbon-containing mixture.

DETAILED DESCRIPTION

Figure 1:
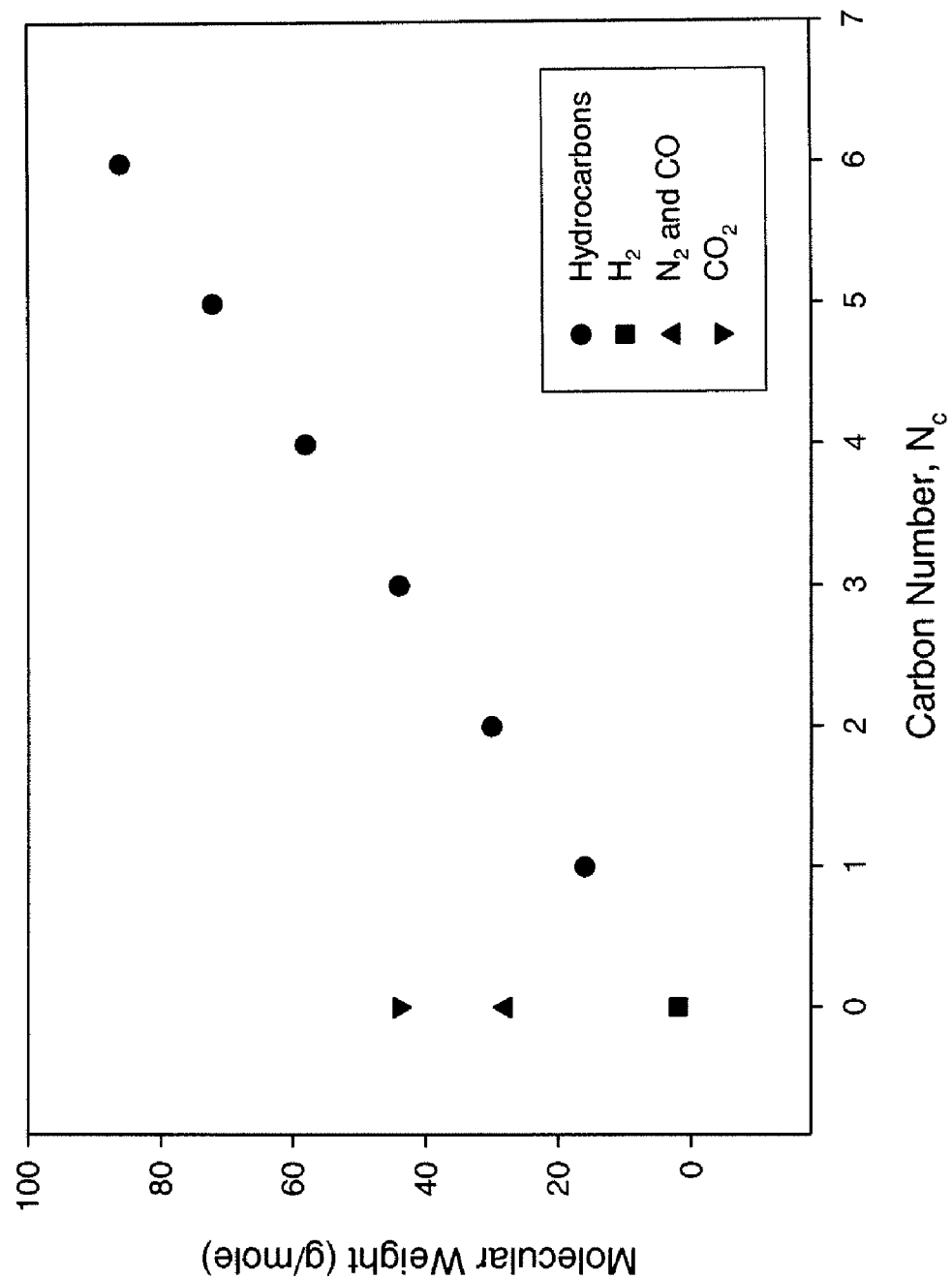
FIG. 1 is a plot of molecular weight versus carbon number.

The indefinite articles "a" and "an" as used herein mean one or more when applied to any feature in embodiments of the present invention described in the specification and claims. The use of "a" and "an" does not limit the meaning to a single feature unless such a limit is specifically stated. The definite article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

For the purposes of simplicity and clarity, detailed descriptions of well-known devices, circuits, and methods are omitted so as not to obscure the description of the present invention with unnecessary detail.

The present invention relates to a method for determining a carbon content value of a hydrocarbon-containing mixture.

A hydrocarbon-containing mixture is a fluid mixture containing at least one hydrocarbon. The hydrocarbon-containing mixture may be formed from natural gas and/or refinery offgas. The hydrocarbon-containing mixture may contain various hydrocarbons, and also non-hydrocarbons such as hydrogen, nitrogen, argon, carbon dioxide, carbon monoxide, water vapor and various other gases.

As used herein, the carbon content of a hydrocarbon-containing mixture is any measure of the relative amount of carbon contained in the hydrocarbon-containing mixture suitable for determining or controlling the steam-to-carbon ratio of a mixed feed for a hydrogen production system. The mole-based carbon number and the mass-based carbon factor are examples of carbon content and are conventional parameters used in the field of hydrogen production and/or synthesis gas production. A mixed feed is any mixture of molecular species suitable for introducing into a hydrogen production process, the mixture formed from at least a hydrocarbon-containing mixture and a steam-containing feed.

As used herein, hydrogen production includes synthesis gas production.

The carbon content value may be a carbon number value. The carbon number, $N_c$, is defined as the total moles of carbon atoms associated with all of the hydrocarbons in one mole of the hydrocarbon-containing mixture. For example, a hydrocarbon-containing mixture containing 90 mole % methane, 5 mole % ethane, and 5 mole % nitrogen would have a carbon number of 1, i.e.

$$\left(90\% \times \frac{1 \text{ mole C}}{1 \text{ mole CH}_4} + 5\% \times \frac{2 \text{ mole C}}{1 \text{ mole C}_2\text{H}_6} + 5\% \times \frac{0 \text{ mole C}}{1 \text{ mole N}_2} = 1.0\right).$$

The carbon content value may be a carbon factor value. The carbon factor, F, is defined as the mass of carbon atoms associated with all of the hydrocarbons per unit mass of the hydrocarbon-containing mixture. For example, a hydrocarbon-containing mixture containing 0.90 mass fraction methane, 0.05 mass fraction ethane, and 0.05 mass fraction nitrogen would have a carbon factor of 0.715, i.e.

$$\left(0.90 \times \frac{12 \text{ g C}}{16 \text{ g CH}_4} + 0.05 \times \frac{24 \text{ g C}}{30 \text{ g C}_2\text{H}_6} + 0.05 \times \frac{0 \text{ g C}}{28 \text{ g N}_2} = 0.715\right).$$

A carbon content value is an express value of carbon content for a particular hydrocarbon-containing mixture composition. For example, the carbon content value for the hydrocarbon-containing mixture containing 90 mole % methane, 5 mole % ethane, and 5 mole % nitrogen is a carbon number of 1.

A composition-dependent bulk property is defined as any intensive physical property of a fluid mixture that varies depending on the concentration of the various mixture components. An intensive property of a fluid mixture is a physical property of the fluid mixture that does not depend on the amount of the fluid mixture. Lower heating value, higher heating value, thermal conductivity, viscosity, molecular weight, density, molar heat capacity, specific heat capacity, and sonic velocity are examples of composition-dependent bulk properties. Suitable composition-dependent bulk properties may be selected without undue experimentation.

A composition-dependent bulk property value is an express value relating to a composition-dependent bulk property for a particular hydrocarbon-containing mixture composition. A composition-dependent bulk property value may be in any suitable units and may be directly proportional or inversely proportional to a value of the composition-dependent bulk property using conventional S.I. units. A composition-dependent bulk property value may also be a value in native form depending on the sensor and/or measurement device used to measure the composition-dependent bulk property. A first composition-dependent bulk property value is an express value relating to a first composition-dependent bulk property for a particular hydrocarbon-containing mixture composition. A second composition-dependent bulk property value is an express value relating to a second composition-dependent bulk property for a particular hydrocarbon-containing mixture composition. A third composition-dependent bulk property value is an express value relating to a third composition-dependent bulk property for a particular hydrocarbon-containing mixture composition.

The higher heating value, also called the gross heating value, is the total heat obtained from combustion of a specified amount of fuel and its stoichiometric correct amount of air, both being at 60° F. when combustion starts, and the combustion products being cooled to 60° F. before the heat release is measured. The units of higher heating value are BTU/μmol or equivalent, for example Joule/kgmol.

The lower heating value, also called the net heating value, is the gross heating value minus the latent heat of vaporization of the water vapor formed by the combustion of components in the fuel that include the element hydrogen, such as hydrogen, methane, propane, etc. Lower heating value is expressed in the same units as higher heating value.

As used herein, a correlation is any mathematical function or equation describing a relationship between variables. A correlation generally describes a dependent variable as function of one or more independent variables.

A carbon content correlation is a correlation of the carbon content as a function of one or more composition-dependent bulk properties and/or concentration of one or more components.

In a first embodiment of the method for determining the carbon content value of a hydrocarbon-containing mixture, the method comprises measuring a first composition-dependent bulk property of the hydrocarbon-containing mixture to determine a first composition-dependent bulk property value. The first composition-dependent bulk property is selected from the group consisting of lower heating value, higher heating value, thermal conductivity, viscosity, molar heat capacity, specific heat capacity, and sonic velocity.

The method according to the first embodiment also comprises calculating the carbon content value using at least the first composition-dependent bulk property value in a carbon content correlation. The carbon content value may be calculated explicitly or as part of another calculation. The first composition-dependent bulk property value is "used" if the carbon content value depends directly or indirectly from the first composition-dependent bulk property value.

Figure 2:
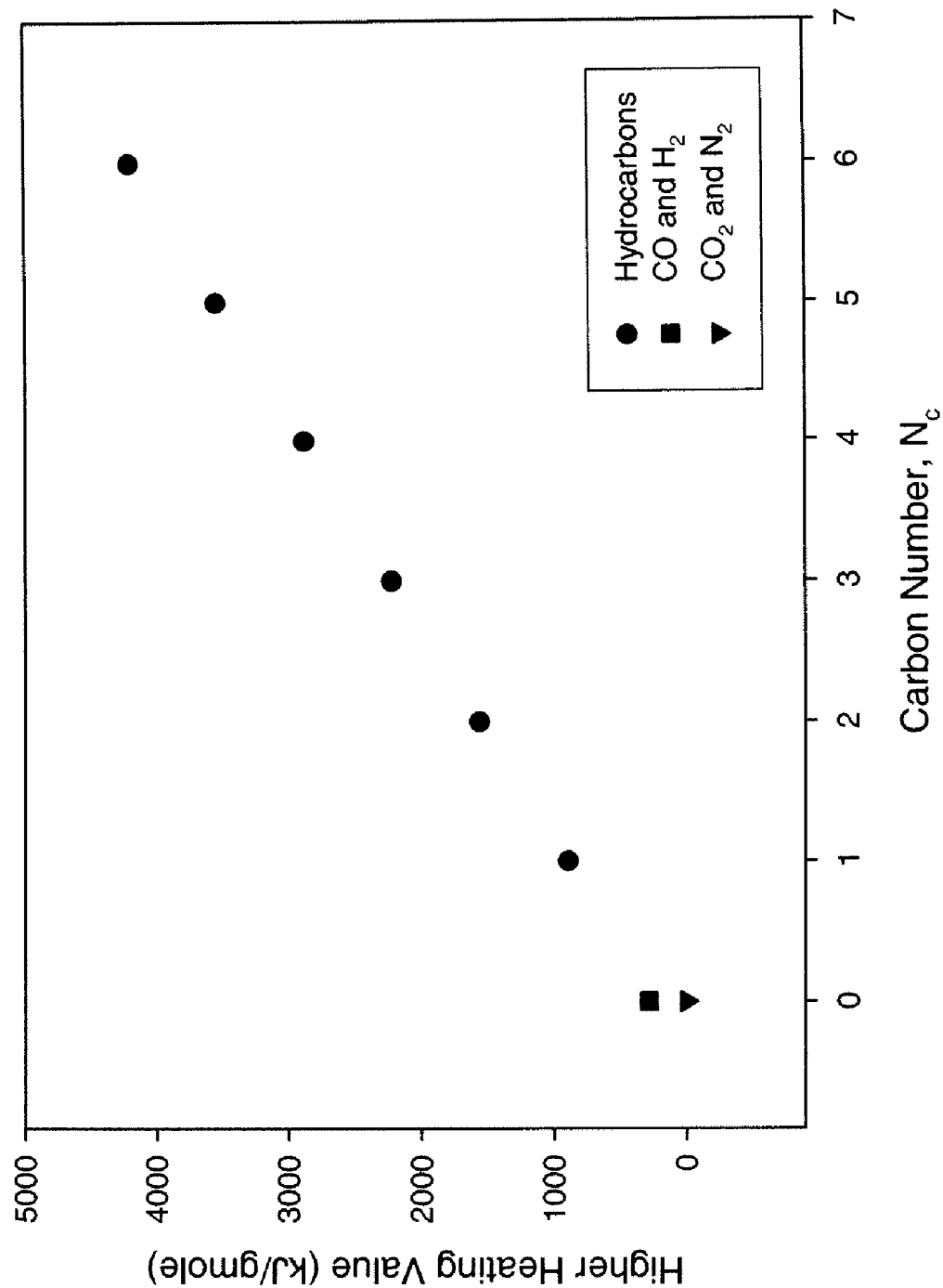
FIG. 2 is a plot of higher heating value versus carbon number.

FIG. 2 shows a plot of higher heating value, HHV, as a function of carbon number, $N_c$, for straight chain alkanes (methane through hexane), hydrogen, carbon monoxide, nitrogen and carbon dioxide. As seen in FIG. 2, hydrogen and carbon monoxide may be conveniently correlated along with the hydrocarbons. If the hydrocarbon-containing mixture contains small or approximately constant amounts of other non-hydrocarbons, higher heating value may be used to provide a suitable correlation for carbon content. The correlation of carbon content and higher heating value can account for the presence of hydrogen and carbon monoxide in the hydrocarbon-containing mixture, independent of the quantity or relative amounts of hydrogen and carbon monoxide. This correlation is particularly suitable for a hydrogen-containing mixture containing large amounts of hydrogen and carbon monoxide, such as refinery offgas.

Figure 3:
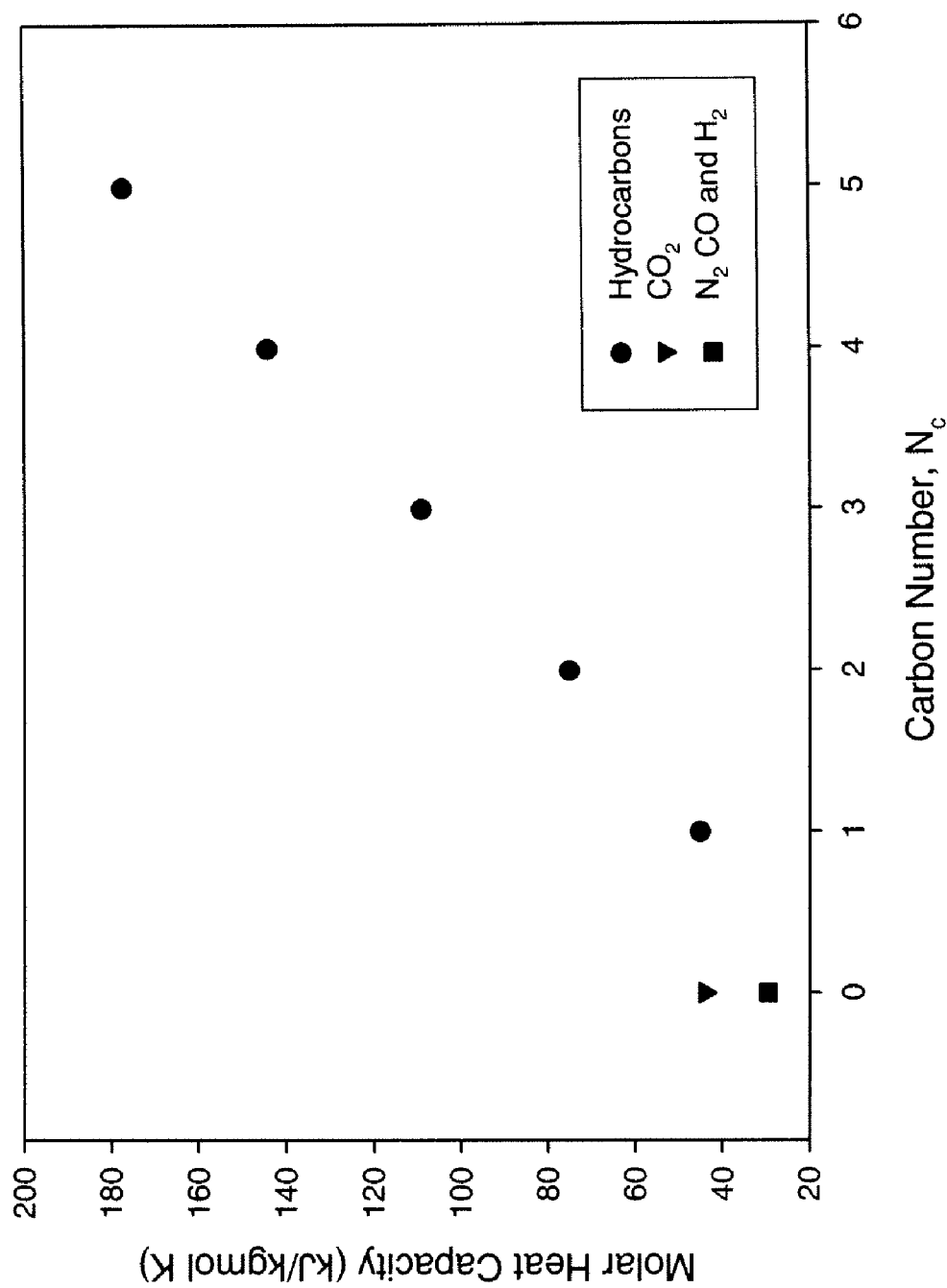
FIG. 3 is a plot of molar heat capacity as a function of carbon number.

FIG. 3 shows a plot of molar heat capacity as a function of carbon number, $N_c$, for straight chain alkanes (methane through hexane), hydrogen, carbon monoxide, nitrogen and carbon dioxide. FIG. 3 shows that hydrogen, carbon monoxide and nitrogen approximately follow the correlation between carbon number and molar heat capacity for hydrocarbons. Hydrogen, carbon monoxide and nitrogen may be conveniently correlated along with the hydrocarbons. If the hydrocarbon-containing mixture contains small or approximately constant amounts of other non-hydrocarbons, molar heat capacity may be used to provide a suitable correlation for carbon content. The correlation of carbon content and molar heat capacity can account for the presence of hydrogen, carbon monoxide and nitrogen in the hydrocarbon-containing mixture, independent of the quantity or relative amounts of hydrogen, carbon monoxide and nitrogen.

A carbon content correlation based on molar heat capacity is especially suitable for hydrocarbon-containing mixtures containing large amounts of hydrogen, carbon monoxide and nitrogen, such as might be found when using refinery offgas, having variable amounts of hydrogen and carbon monoxide, or using natural, having variable amounts of nitrogen. A carbon content correlation based on molar heat capacity may still be useful for hydrocarbon-containing mixtures containing carbon dioxide, provided the concentration of carbon dioxide is small or approximately constant.

Figure 4:
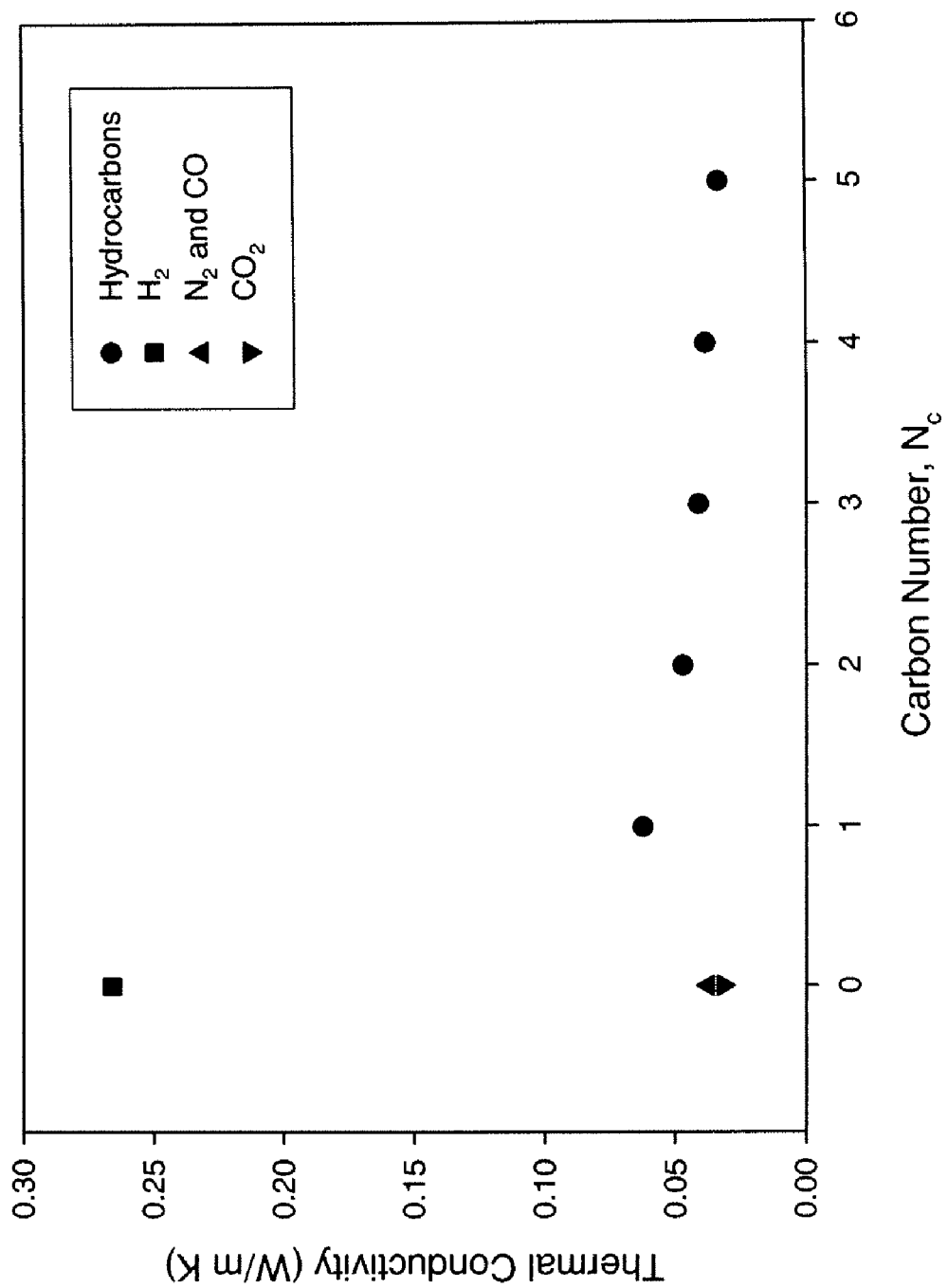
FIG. 4 is a plot of thermal conductivity as a function of carbon number.

FIG. 4 shows a plot of thermal conductivity as a function of carbon number, $N_c$, for straight chain alkanes (methane through hexane), hydrogen, carbon monoxide, nitrogen and carbon dioxide. There may be special situations where a carbon content correlation based on thermal conductivity is useful, for example when the total concentration of carbon monoxide, carbon dioxide and nitrogen is sufficiently constant and only the proportion of these components varies. A carbon content correlation based on thermal conductivity may also be useful when the hydrogen concentration is sufficiently constant.

Figure 5:
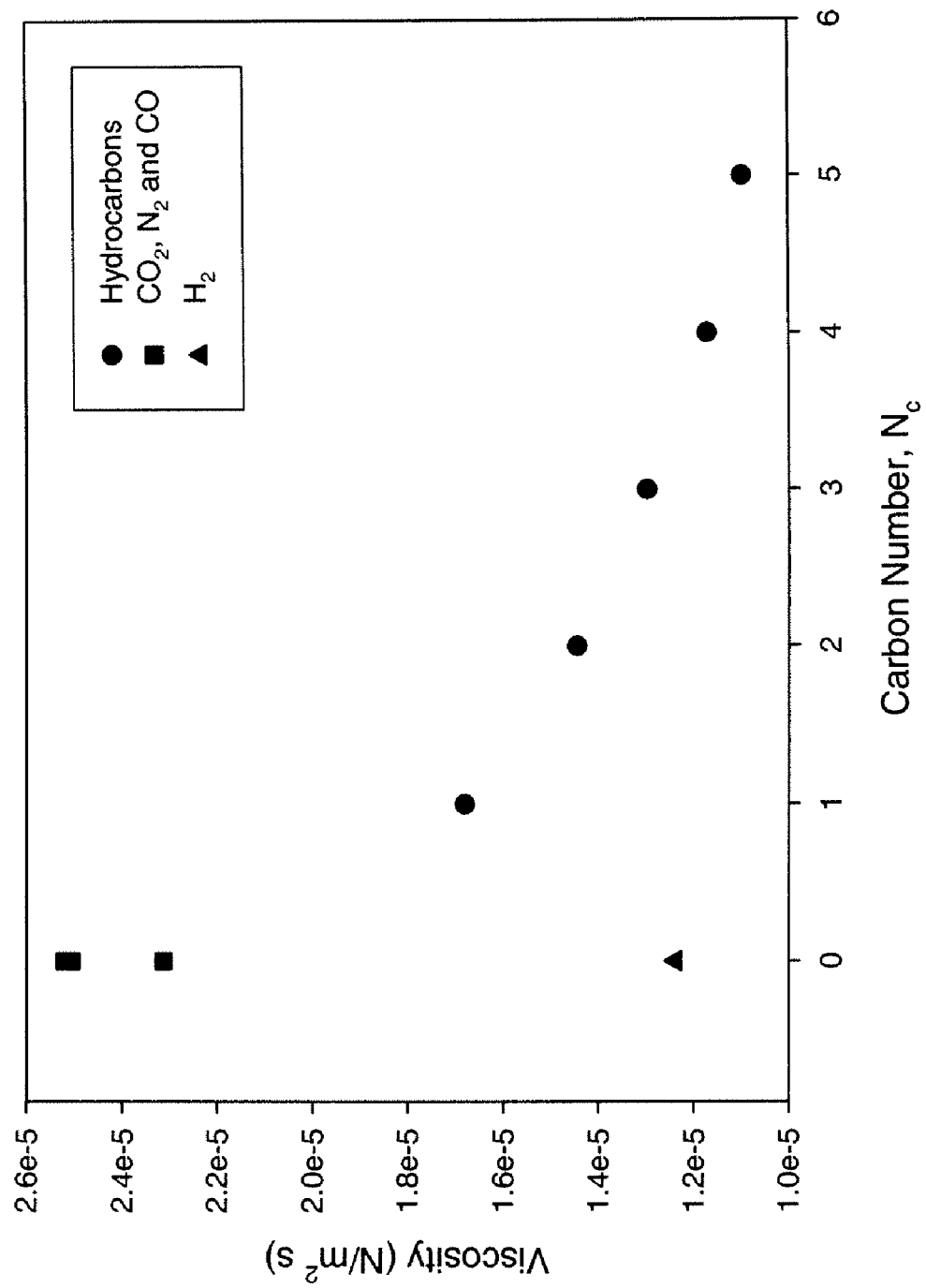
FIG. 5 is a plot of viscosity as a function of carbon number.

FIG. 5 shows a plot of viscosity as a function of carbon number, $N_c$, for straight chain alkanes (methane through hexane), hydrogen, carbon monoxide, nitrogen and carbon dioxide. Carbon monoxide, carbon dioxide and nitrogen may be conveniently correlated along with the hydrocarbons. If the hydrocarbon-containing mixture contains small or approximately constant amounts of other non-hydrocarbons, viscosity may be used to provide a suitable correlation for carbon content. The correlation of carbon content and viscosity can account for the presence of carbon monoxide, carbon dioxide and nitrogen in the hydrocarbon-containing mixture, independent of the quantity or relative amounts of carbon monoxide, carbon dioxide and nitrogen.

Figure 6:
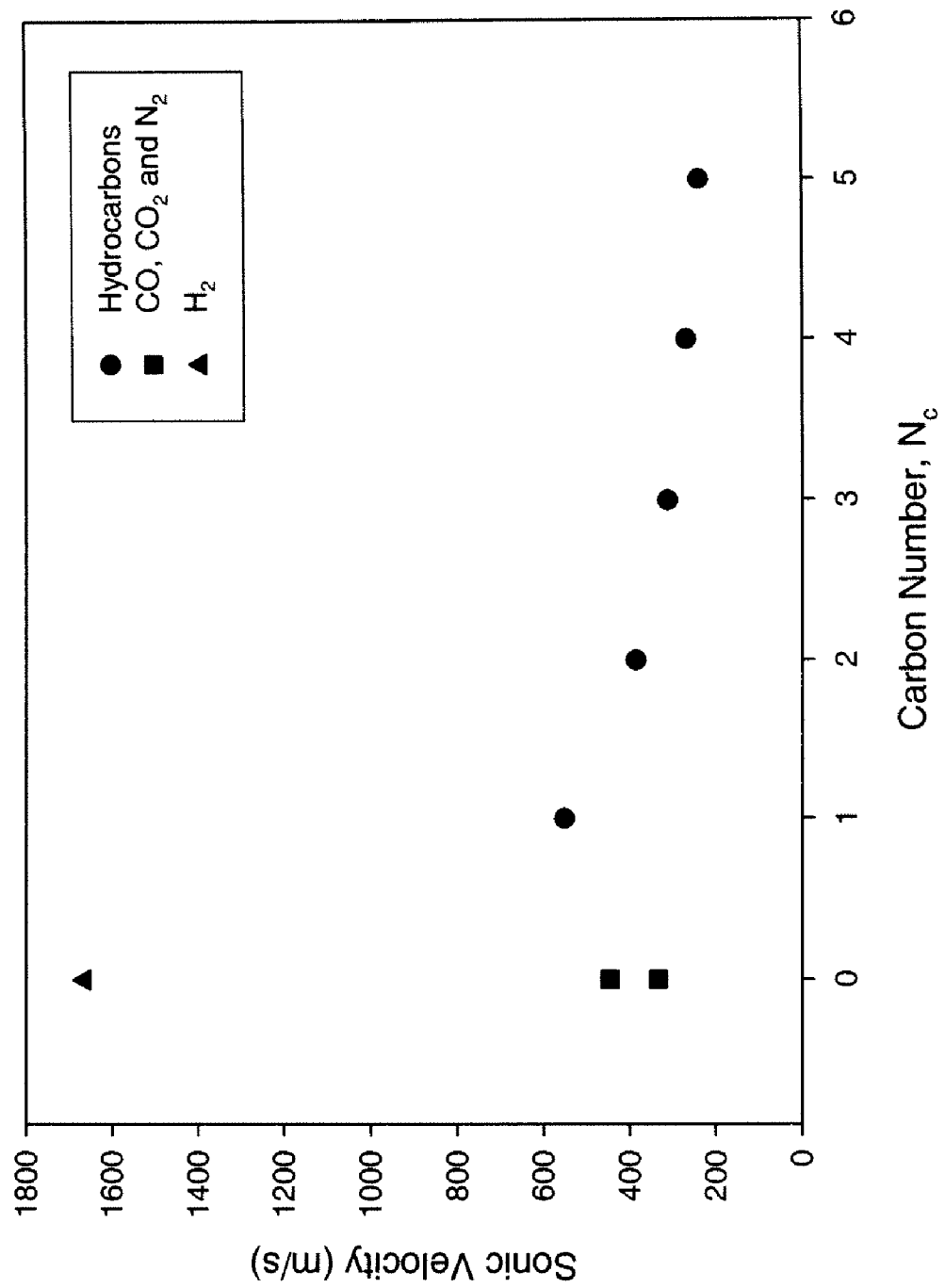
FIG. 6 is a plot of sonic velocity as a function of carbon number

FIG. 6 shows a plot of sonic velocity as a function of carbon number, $N_c$, for straight chain alkanes (methane through hexane), hydrogen, carbon monoxide, nitrogen and carbon dioxide. A carbon content correlation based on sonic velocity may be useful for hydrocarbon-containing mixtures for special situations.

In a second embodiment of the method for determining the carbon content value of a hydrocarbon-containing mixture, the method comprises containing a fixed mass of a reference gas in a fixed-volume enclosure where the reference gas has a reference gas temperature and a reference gas pressure. The reference gas may be any suitable gas where the molecular weight is known. The reference gas may be a gas mixture or pure component. The molecular weight may be determined by measuring the mole fractions of the various mixture components and calculating the molecular weight of the mixture using a suitable mixture rule. When the hydrocarbon-containing mixture contains mainly methane, the reference gas may be methane. It is desirable to use a reference gas having a similar compressibility factor, Z, as the hydrocarbon-containing mixture.

As used herein, a fixed-volume enclosure is an enclosure whose volume changes by less than 1% of an initial volume upon charging with reference gas.

The method according to the second embodiment further comprises measuring the density of the hydrocarbon-containing mixture to determine a density value of the hydrocarbon-containing mixture at a first temperature and a first pressure where the first temperature equal to the reference gas temperature and the first pressure equal to the reference gas pressure. As used herein, the first temperature is equal to the reference gas temperature if it is within 2° C. of the reference gas temperature as measured by a calibrated thermocouple, for example a 100 ohm platinum, alpha 0.00385 ohms/ohm/deg C resistance temperature device (RTD) such as available from Rosemount. As used herein, the first pressure is equal to the reference gas pressure if it is within 7 kPa of the reference gas pressure as measured by a calibrated pressure transducer, for example a Rosemount 3051 or 1151. It is not necessary to measure the temperature or pressure of the hydrocarbon-containing mixture or to measure the temperature or pressure of the reference gas in order to carry out the method according to the second embodiment.

The temperature of the hydrocarbon-containing mixture may be made equal to the reference gas temperature by any means, for example by putting the hydrocarbon-containing mixture in heat transfer communication with the reference gas. The pressure of the hydrocarbon-containing mixture may be made equal to the reference gas pressure by any means known in the art, for example by suitable flow restrictions and/or diaphragms. U.S. Pat. No. 3,916,672 discloses a device for making the temperature of the hydrocarbon-containing mixture equal to the reference gas temperature and the pressure of the hydrocarbon-containing mixture equal to the reference gas pressure.

The device of U.S. Pat. No. 3,916,672 maintains the temperature and pressure of the hydrocarbon-containing mixture equal to the reference gas, irrespective of variations in the pressure of the supply from which the hydrocarbon-containing mixture is obtained. Ambient temperature variations affect the reference gas and the hydrocarbon-containing mixture equally and therefore have no effect on the density measurement, since the effect on the density measurement of the pressure change in the hydrocarbon-containing mixture caused by the temperature change in the reference gas is compensated by the effect of the temperature change of the sample gas in the conduit.

The density value may be obtained from any suitable density sensitive device that produces an output signal representative of the gas density. The density value may be determined by any suitable densitometer known in the art, for example a vibrating element sensor, a capacitive sensor or a nucleonic sensor. The densitometer may be a vibrating tube densitometer.

A vibrating element sensor is defined as any sensor that has a vibrating structure. It is known that, in a vibration densitometer, if a structure is vibrated at its resonant frequency while being immersed in a fluid, the density of the said fluid can be determined by measuring the resonant frequency. The vibrating element may be a vane as described in U.S. Pat. No. 3,677,067, a tuning fork as described in U.S. Pat. No. 4,526,480, a cylinder as described in U.S. Pat. No. 6,029,501, a double-bar double-ended resonator or double-bar single-ended as described in U.S. Pat. No. 4,535,638, or any other vibrating element known in the art. The vibrating element, for example a tuning fork and vane, may be surrounded by the fluid to be measured or the fluid may flow inside of the vibrating element, for example a tube. Examples of vibrating element sensors are also illustrated in U.S. Pat. Nos. 3,426,593, 3,715,912, 4,574,639, 4,644,796, 4,644,803.

A capacitive sensor is defined as any sensor that senses a fluid's dielectric properties. Examples of capacitive sensors are illustrated in U.S. Pat. Nos. 3,421,077, 3,903,478, 4,835,456, and 5,027,076.

A nucleonic sensor is defined as any sensor that uses a radiation source and detector. The radiation may be x-ray as in U.S. Pat. No. 4,277,681, gamma-ray (y-ray) as in U.S. Pat.

Nos. 5,166,964 and 2,898,466, neutrons as in U.S. Pat. No. 4,582,991, beta-ray as in U.S. Pat. No. 2,757,290 or other radiation source known in the art. Nucleonic, also called radiation type, sensors are also discussed in U.S. Pat. Nos. 2,763,790, 2,968,729, 2,922,888, 3,196,271, and 6,548,814.

A density value is an express value directly relating to the density of a particular hydrocarbon-containing mixture composition. The density value may be in any suitable units and may be directly proportional or inversely proportional to a value of the density using conventional S.I. units. The density value may also be a value in native form depending on the sensor and/or measurement device used to measure the density. For example, if a vibrating tube densitometer is used, the density value may be expressed as a frequency (Hz).

The usefulness of determining the density value at the same temperature and pressure as the reference gas will become apparent from the following discussion.

The specific gravity, SG, is defined $$SG = \frac{\rho_s}{\rho_r} \quad \text{(Equation 1)}$$

where $\rho_s$ is the density of the sample (hydrocarbon-containing mixture) and $\rho_r$ is the density of the reference gas.

For gases:

$$\rho = M\frac{n}{V} = M\frac{P}{RTZ} \quad \text{(Equation 2)}$$

where M is molecular weight, n is the number of moles of the gas, V is the volume, P is pressure, R is the gas constant, T is temperature, and Z is the compressibility factor.

Substituting equation 2 into equation 1 for the sample gas and the reference gas gives:

$$SG = \frac{\rho_s}{\rho_r} = \frac{P_s M_s T_r Z_r}{P_r M_r T_s Z_s} \quad \text{(Equation 3)}$$

where the subscript s represent the property for the sample gas and the subscript r represents the property for the reference gas.

As per the method according to the second embodiment, the density of the hydrocarbon-containing mixture (sample gas) is measured at the same temperature as the reference gas temperature, $T_r = T_s$. Also the density of the hydrocarbon-containing mixture is measured at the same pressure as the reference gas pressure, $P_r = P_s$. As discussed earlier, it is desirable to select a reference gas having essentially the same compressibility factor as the hydrocarbon-containing mixture, then $Z_r = Z_s$. In this case, $$SG = \frac{M_s}{M_r}. \quad \text{(Equation 4)}$$

For the reference gas, the density $\rho_r$ is constant since the molecular weight is known and fixed, the mass amount is fixed and constant, and the volume is fixed and constant. Let the density be represented by the constant $$\frac{1}{K_r}.$$

Substituting equation 4 and $$\rho_r = \frac{1}{K_r}$$

into equation 1 gives:

$$M_s = M_r K_r \rho_s \quad \text{(Equation 5)}$$

The molecular weight of the hydrocarbon-containing mixture is proportional to the density value of the hydrocarbon-containing mixture.

The method according to the second embodiment also comprises calculating the carbon content value using at least the density value in a carbon content correlation. The carbon content value may be calculated explicitly or as part of another calculation. The density value is "used" if the carbon content value depends directly or indirectly from the density value.

The method according to the first embodiment and the method according to the second embodiment may further comprise measuring a concentration of at least one non-hydrocarbon component to determine a non-hydrocarbon component concentration value. In the step of calculating the carbon content value, the non-hydrocarbon component concentration value is used in the carbon content correlation when the concentration of at least one non-hydrocarbon component is measured. The at least one non-hydrocarbon component may be selected from nitrogen, carbon monoxide and carbon dioxide.

The concentration of various non-hydrocarbon species may be measured using various means. For example, for hydrogen, COSA/Xentaur offers a commercial Continuous Hydrogen Analyzer (CHA). The device has an electrochemical sensor that produces a continuous signal corresponding directly to the hydrogen concentration. For carbon monoxide and/or carbon dioxide, Servomex offers a continuous analyzer, for example the Servomex 1440 Gas Analyzer, that uses a single beam, single wavelength infrared technology to selectively measure carbon monoxide and/or carbon dioxide. For nitrogen, hydrogen, carbon monoxide, and/or carbon dioxide, a gas chromatograph may be used to measure the concentrations of these components. Gas chromatographs are offered by a number of companies, including Perkin Elmer. U.S. Pat. No. 7,010,433 also discloses measuring nitrogen and carbon dioxide concentrations in a hydrocarbon-containing mixture.

A carbon content correlation that uses non-hydrocarbon component concentration values may be formulated in a variety of ways.

A carbon number correlation may be formulated for hydrocarbons and other components that may be conveniently grouped with the hydrocarbons. For example, hydrogen and carbon monoxide may be conveniently grouped with the hydrocarbons in a correlation that uses higher heating value. The remaining components, in this example nitrogen and carbon dioxide, are considered outlier components. In the method according to the second embodiment, for example, hydrogen may be conveniently grouped with the hydrocarbons in a correlation that uses molecular weight or density.

The remaining components, in this example nitrogen, carbon monoxide, and carbon dioxide, are considered outlier components. The correlation for the hydrocarbons and non-outlier components is herein referred to as the principal carbon number correlation, may be written:

$$N_c^o = a_1 \times P_{HC} + c_1 \quad \text{(Equation 6)}$$

where $N_c^o$ is the principal carbon number, $P_{HC}$ is a composition-dependent bulk property for the hydrocarbon components and non-outlier components, $a_1$ is a coefficient determined by regression analysis, and $c_1$ is a constant determined by regression analysis.

Composition-dependent bulk properties may be approximated by various mixing rules, for example:

$$P = \left(1 - \sum_i y_i\right) \times P_{HC} + \sum_i y_i \times P_i \quad \text{(Equation 7)}$$

where P is the composition dependent bulk property of the entire mixture, $y_i$ is the mole fraction of outlier component i, and $P_i$ is the pure component property value for outlier component i.

The carbon number of the hydrocarbon-containing mixture may be calculated from $$N_c = \left(1 - \sum_i y_i\right) \times N_c^o \quad \text{(Equation 8)}$$

Substituting and rearranging gives the carbon number as a function of the measured composition dependent bulk property, P, and mole fractions of outlier components, $y_i$:

$$N_c = a_1 \times \left(P - \sum_i y_i P_i\right) + c_1 \times \left(1 - \sum_i y_i\right) \quad \text{(Equation 9)}$$

Equation 9 can then be used to calculate the carbon number from a measurement of the composition-dependent bulk property and the mole fraction of the one or more outlier species.

Alternative methods for using the non-hydrocarbon species concentration value in the carbon content correlation may also be formulated. The example above is meant for illustration purposes and not intended to limit the scope of the claims.

The method according to the first embodiment and the method according to the second embodiment may further comprise measuring a second composition-dependent bulk property of the hydrocarbon-containing mixture to determine a second composition-dependent bulk property value. In the step of calculating the carbon content value, the second composition-dependent bulk property value is used in the carbon content correlation when the second composition dependent bulk property is measured.

In the first embodiment of the method, the second composition-dependent bulk property is a different composition-dependent bulk property than the first composition-dependent bulk property. For example if the first composition-dependent bulk property is chosen to be higher heating value, the second composition-dependent bulk property is not the higher heating value. Suitable pairs of composition-dependent bulk properties may be selected without undue experimentation.

In the second embodiment of the method, the second composition-dependent bulk property is a different composition-dependent bulk property than density or molecular weight. In the second embodiment of the method, density or molecular weight is the first composition-dependent bulk property. The second composition-dependent bulk property may be selected from the group consisting of lower heating value, higher heating value, thermal conductivity, viscosity, molar heat capacity, specific heat capacity, and sonic velocity. Suitable composition-dependent bulk properties may be selected without undue experimentation.

Measurement of composition-dependent bulk properties may be by any suitable sensor known in the art. For example, heating value may be measured by COSA Instrument Corporation's COSA 9600. Thermal conductivity may be measured by Servomex K1550 thermal conductivity analyzer. Heat capacity may be measured by calorimetry measurements and/or speed of sound measurements with a Kundt's tube. Viscosity may be measured by a capillary viscometer. Measurement of sonic velocity is disclosed in U.S. Pat. No. 5,467,637. The skilled person is capable of selecting suitable sensors.

Bulk property measurements may be by direct or inferred techniques. Measuring includes any step for producing an output signal representative of the bulk property. For example, density may be measured by actually measuring the frequency of a vibrating tube, as in a vibrating tube densitometer. The composition-dependent bulk property value may be a frequency which directly relates to the density of the hydrocarbon-containing mixture. In another of several alternatives, the frequency can be used to calculate the density of the hydrocarbon-containing mixture in conventional S.I. units.

The method according to the first embodiment may comprise calculating the carbon content value using at least the first composition-dependent bulk property value and the second composition-dependent bulk property value in a carbon content correlation. The carbon content value may be calculated explicitly or as part of another calculation. The first composition-dependent bulk property value and the second composition-dependent bulk property value are "used" if the carbon content value depends directly or indirectly from the first composition-dependent bulk property value and the second composition-dependent bulk property value.

The method according to the second embodiment may comprise calculating the carbon content value using at least the density value and the second composition-dependent bulk property value in a carbon content correlation. The carbon content value may be calculated explicitly or as part of another calculation. The density value and the second composition-dependent bulk property value are "used" if the carbon content value depends directly or indirectly from the density value and the second composition-dependent bulk property value.

The carbon content correlation may be related to two or more composition-dependent bulk properties. For ease of application, the carbon content correlation may describe the carbon content as the dependent variable and the two or more composition dependent bulk properties as independent variables.

In the method according to the first embodiment, the carbon content correlation may be a function of the first composition-dependent bulk property and the second composition-dependent bulk property. The carbon content correlation may be a single function describing the relationship between the carbon content and the first composition-dependent bulk property and the second composition-dependent bulk property.

In the method according to the second embodiment, the carbon content correlation may be a function of the density or molecular weight and the second composition-dependent bulk property. The carbon content correlation may be a single function describing the relationship between the carbon content and the density or molecular weight and the second composition-dependent bulk property.

In the method according to the first embodiment, the carbon content correlation may comprise a multivariable function of the first composition-dependent bulk property and the second composition-dependent bulk property and optionally additional composition-dependent bulk properties.

In the method according to the second embodiment, the carbon content correlation may comprise a multivariable function of the density or molecular weight and the second composition-dependent bulk property and optionally additional composition-dependent bulk properties.

A multivariable function is a function where an independent variable is not related by separate and independent functions of various dependent variables. A separate function is a function relating an independent variable to one dependent variable without taking into account other dependent variables. For example, the carbon content could be correlated with the first composition-dependent bulk property and separately correlated with the second composition-dependent bulk property. This example would not represent a multivariable function.

In the method according to the first embodiment, the carbon content correlation may be a linear function of the first composition-dependent bulk property and a linear function of the second composition-dependent bulk property. For example, the carbon content, expressed in terms of a carbon number $N_c$ may have the functional form:

$$N_c = b_1 \times P + b_2 \times Q + b_3 \quad \text{(Equation 10)}$$

where P is the first composition-dependent bulk property, Q is the second composition-dependent bulk property, $b_1$ and $b_2$ are coefficients determined by regression analysis, and $b_3$ is a constant determined by regression analysis.

This linear function is an example of a multivariable function. The carbon content is related to the first composition-dependent bulk property and the second composition-dependent bulk property in the same equation.

In the method according to the second embodiment, the carbon content correlation may be a linear function of the density or molecular weight and a linear function of the second composition-dependent bulk property. In this case, P in equation 10 is the density or molecular weight.

A carbon content correlation may be produced in a number of different ways. The carbon content correlation may be produced using actual samples of hydrocarbon-containing mixtures from a hydrogen production process and actual measurements of composition-dependent bulk properties of those samples. The carbon content correlation may be produced using actual samples of hydrocarbon-containing mixtures and bulk property simulations. The carbon content correlation may be produced using hypothetical samples of hydrocarbon-containing mixtures and bulk property simulations.

For the method according to the first embodiment, the carbon content correlation may be produced by: taking a plurality of hydrocarbon-containing mixture samples; determining the carbon content value of the plurality of hydrocarbon-containing mixture samples by compositional analysis, thereby forming a carbon content value array; measuring a first composition-dependent bulk property for the plurality of hydrocarbon-containing mixture samples to obtain a first composition-dependent bulk property value array; optionally measuring a second composition-dependent bulk property for the plurality of hydrocarbon-containing mixture samples to obtain an optional second composition-dependent bulk property value array; and correlating the carbon content value array with the first composition-dependent bulk property value array and optionally the second composition-dependent bulk property value array to form the carbon content correlation. The carbon content correlation may be in the form of a multivariable function of the first composition-dependent bulk property and the second composition-dependent bulk property.

For the method according to the second embodiment, the carbon content correlation may be produced by: taking a plurality of hydrocarbon-containing mixture samples; determining the carbon content value of the plurality of hydrocarbon-containing mixture samples by compositional analysis, thereby forming a carbon content value array; measuring a density for the plurality of hydrocarbon-containing mixture samples to obtain a density value array; and correlating the carbon content value array with the density value array to form the carbon content correlation.

For the case where a second composition-dependent bulk property is used in the second embodiment, the carbon content correlation may be produced by: taking a plurality of hydrocarbon-containing mixture samples; determining the carbon content value of the plurality of hydrocarbon-containing mixture samples by compositional analysis, thereby forming a carbon content value array; measuring a density for the plurality of hydrocarbon-containing mixture samples to obtain a density value array; measuring a second composition-dependent bulk property for the plurality of hydrocarbon-containing mixture samples to obtain a second composition-dependent bulk property value array; and correlating the carbon content value array with the density value array and the second composition-dependent bulk property value array to form the carbon content correlation. The carbon content correlation may be in the form of a multivariable function of the density and the second composition-dependent bulk property.

Data for generating the correlation may be obtained from the hydrogen production facility. A sensor for measuring the first composition-dependent bulk property or density and optionally a sensor for measuring the second composition-dependent bulk property may measure the hydrocarbon-containing mixture in-situ, and a sample collected for compositional analysis offline. Alternatively, samples may be collected with measurements and analysis done offline.

For the method according to the first embodiment, the carbon content correlation may be produced by: taking a plurality of hydrocarbon-containing mixture samples from a hydrogen production facility; determining sample composition and the carbon content value of the plurality of hydrocarbon-containing mixture samples by compositional analysis, thereby forming a carbon content value array; calculating a first composition-dependent bulk property value array using a bulk property simulation of the sample composition from the compositional analysis; calculating a second composition-dependent bulk property value array using a bulk property simulation of the sample composition from the compositional analysis; and correlating the carbon content value array with the first composition-dependent bulk property value array and the second composition-dependent bulk property value array to form the carbon content correlation. The carbon content correlation may be in the form of a multivariable function of the first composition-dependent bulk property and the second composition-dependent bulk property.

For the method according to the second embodiment, the carbon content correlation may be produced by: taking a plurality of hydrocarbon-containing mixture samples from a hydrogen production facility; determining sample composition and the carbon content value of the plurality of hydrocarbon-containing mixture samples by compositional analysis, thereby forming a carbon content value array; calculating a density value array using a bulk property simulation of the sample composition from the compositional analysis; and correlating the carbon content value array with the density value array and to form the carbon content correlation.

For the method according to the second embodiment, the carbon content correlation may be produced by: taking a plurality of hydrocarbon-containing mixture samples from a hydrogen production facility; determining sample composition and the carbon content value of the plurality of hydrocarbon-containing mixture samples by compositional analysis, thereby forming a carbon content value array; calculating a density value array using a bulk property simulation of the sample composition from the compositional analysis; calculating a second composition-dependent bulk property value array using a bulk property simulation of the sample composition from the compositional analysis; and correlating the carbon content value array with the density value array and the second composition-dependent bulk property value array to form the carbon content correlation. The carbon content correlation may be in the form of a multivariable function of the density and the second composition-dependent bulk property.

The plurality of hydrocarbon-containing mixture samples may cover the broadest range of expected compositions in order to provide the most suitable correlation.

For the method according to the first embodiment, the carbon content correlation may be produced by: specifying a plurality of hypothetical mixture compositions representing a suitable range of expected mixture compositions from a hydrogen production facility; calculating the carbon content value of the plurality of hypothetical mixture compositions, thereby forming a carbon content value array; calculating a first composition-dependent bulk property value array using a bulk property simulation of the plurality of hypothetical mixture compositions; calculating a second composition-dependent bulk property value array using a bulk property simulation of the plurality of hypothetical mixture compositions; and correlating the carbon content value array with the first composition-dependent bulk property value array and the second composition-dependent bulk property value array to form the carbon content correlation. The carbon content correlation may be in the form of a multivariable function of the first composition-dependent bulk property and the second composition-dependent bulk property.

For the method according to the second embodiment, the carbon content correlation may be produced by: specifying a plurality of hypothetical mixture compositions representing a suitable range of expected mixture compositions from a hydrogen production facility; calculating the carbon content value of the plurality of hypothetical mixture compositions, thereby forming a carbon content value array; calculating a density value array using a bulk property simulation of the plurality of hypothetical mixture compositions; and correlating the carbon content value array with the density value array to form the carbon content correlation.

For the method according to the second embodiment, the carbon content correlation may be produced by: specifying a plurality of hypothetical mixture compositions representing a suitable range of expected mixture compositions from a hydrogen production facility; calculating the carbon content value of the plurality of hypothetical mixture compositions, thereby forming a carbon content value array; calculating a density value array using a bulk property simulation of the plurality of hypothetical mixture compositions; calculating a second composition-dependent bulk property value array using a bulk property simulation of the plurality of hypothetical mixture compositions; and correlating the carbon content value array with the density value array and the second composition-dependent bulk property value array to form the carbon content correlation. The carbon content correlation may be in the form of a multivariable function of the density and the second composition-dependent bulk property.

Correlating may be by any known regression routine, for example, linear least squares regression. Regression routines are readily available. Data may be weighted differently, if desired.

Figure 7:
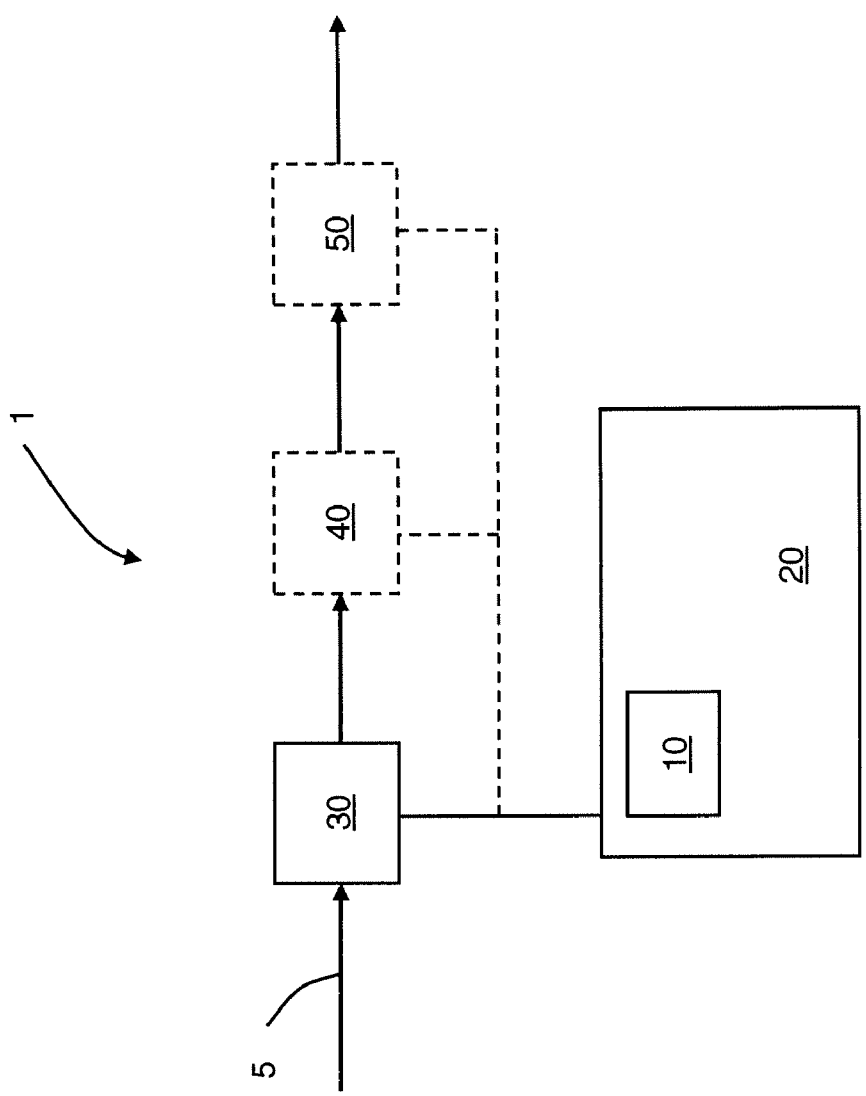
FIG. 7 is a schematic of an exemplary apparatus for performing a method for determining a carbon content value of a hydrocarbon-containing mixture.

Referring now to the drawings, wherein like reference numbers refer to like elements throughout the figures, FIG. 7 shows a schematic of an exemplary apparatus 1 for performing the method for determining a carbon content value of a hydrocarbon-containing mixture according to the first embodiment. Hydrocarbon-containing mixture 5 is sampled by sensor 30 for measuring a first composition-dependent bulk property. Sensor 30 measures one of lower heating value, higher heating value, thermal conductivity, viscosity, molar heat capacity, specific heat capacity and sonic velocity. Sensor 30 sends a signal to computer 20 and a first composition-dependent bulk property value is determined.

Optionally, hydrocarbon-containing mixture 5 is sampled by optional sensor 40 for measuring a second composition-dependent bulk property. In this instance, optional sensor 40 sends a signal to computer 20 and a second composition-dependent bulk property value is determined. Optionally, hydrocarbon-containing mixture 5 is sampled by optional sensor 50 for measuring a concentration of at least one non-hydrocarbon component in the hydrocarbon-containing mixture. In this instance, optional sensor 50 sends a signal to computer 20 and a non-hydrocarbon component concentration value is determined. Computer 20 has a carbon content correlation 10 for calculating a carbon content value as a function of composition-dependent bulk properties and/or non-hydrocarbon component concentrations. Computer 20 calculates the carbon content value using the first composition-dependent bulk property value and optionally the second composition-dependent bulk property value and optionally the non-hydrocarbon component concentration value in carbon content correlation 10. The carbon content value can then be used by the hydrogen production process to generate a desired steam-to-carbon ratio.

Sensor 30, optional sensor 40 and optional sensor 50 may be oriented in a variety of ways. Sensor 30, optional sensor 40, and optional sensor 50 may be mounted in the conduit containing the hydrocarbon-containing mixture. Alternatively, one or more slip streams may be taken from the conduit containing the hydrocarbon-containing mixture. Sensor 30, optional sensor 40 and optional sensor 50 may be mounted to measure the one or more slip streams. The slip stream may be conditioned, for example where the temperature and/or pressure are modified from the conditions of the process stream. In another alternative, one or more of sensor 30, optional sensor 40 and optional sensor 50 may be mounted in the conduit containing the hydrocarbon-containing mixture and the remaining sensor(s) mounted to measure a slip stream.

The first embodiment of the method for determining a carbon content value of a hydrocarbon-containing mixture including one or more of the various features may be used in a method for producing a mixed feed for hydrogen production.

Figure 8:
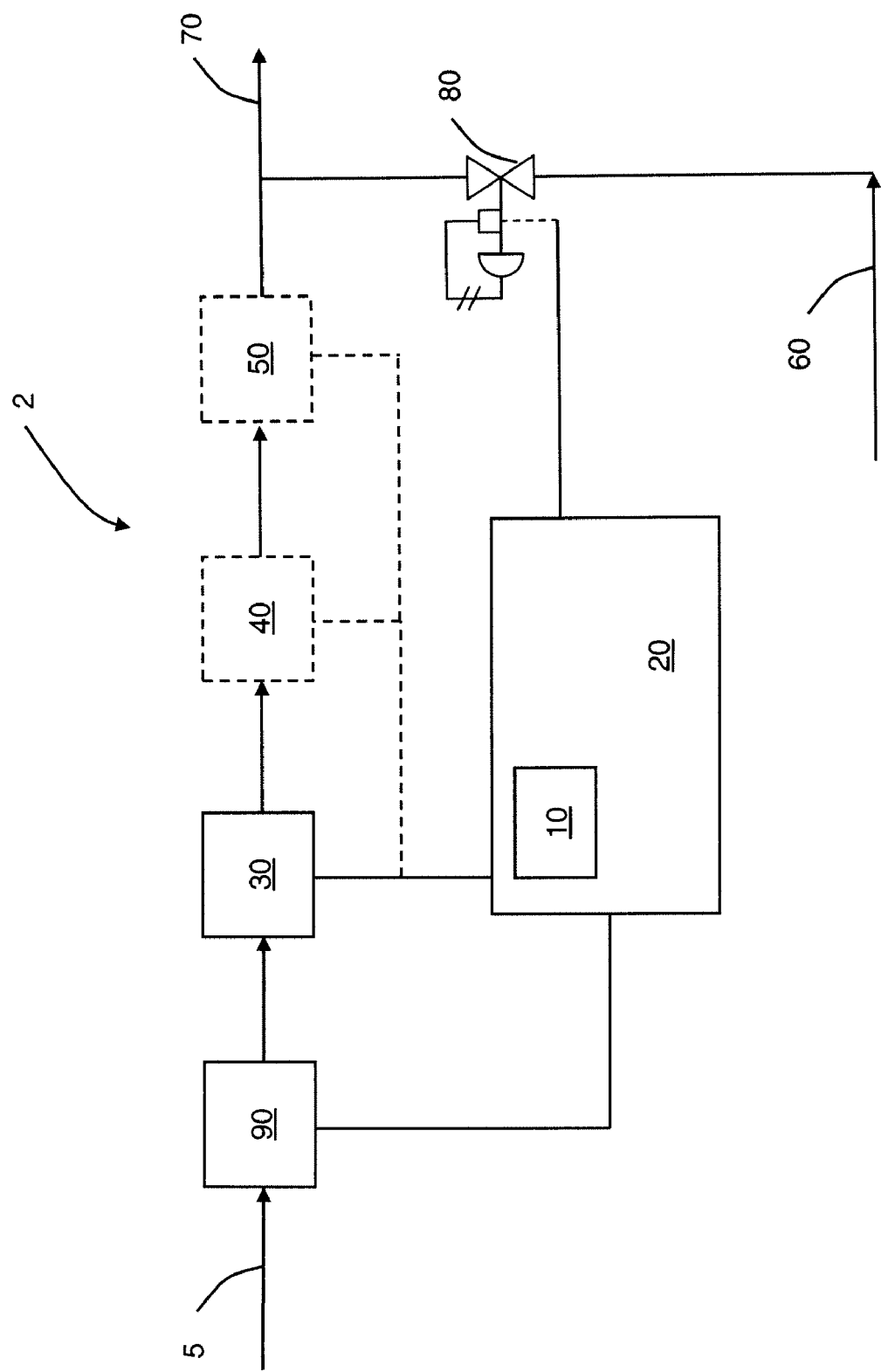
FIG. 8 is a schematic of an exemplary apparatus for performing a method for producing a mixed feed.

The method for producing a mixed feed for hydrogen or synthesis gas production using the first embodiment of the method for determining the carbon content value of a hydrocarbon-containing mixture is described with reference to FIG. 8. FIG. 8 shows a schematic of an exemplary apparatus 2 for performing the method for producing a mixed feed.

The method for producing a mixed feed using the first embodiment of the method for determining the carbon content value comprises measuring a flow rate of a hydrocarbon-containing mixture thereby obtaining a measured flow rate. As shown in FIG. 8, the flow rate of the hydrocarbon-containing mixture is measured by flowmeter 90 and flowmeter 90 sends a signal to computer 20 indicative of the flow rate. Suitable devices for measuring flow rate are known in the art.

The method for producing a mixed feed also comprises measuring a first composition-dependent bulk property of the hydrocarbon-containing mixture to determine a first composition-dependent bulk property value, optionally measuring a second composition-dependent bulk property of the hydrocarbon-containing mixture to determine a second composition-dependent bulk property value, and optionally measuring a concentration of at least one non-hydrocarbon component in the hydrocarbon-containing mixture to determine a non-hydrocarbon component concentration value. As shown in FIG. 8, hydrocarbon-containing mixture 5 is sampled by sensor 30 for measuring a first composition-dependent bulk property, optionally sampled by sensor 40 for measuring a second composition-dependent bulk property, and optionally sampled by sensor 50 for measuring a concentration of at least one non-hydrocarbon component. Sensor 30, and optionally sensor 40 and sensor 50 send signals to computer 20 and a first composition-dependent bulk property value and optionally a second composition-dependent bulk property value and non-hydrocarbon component concentration value are determined.

The method for producing the mixed feed further comprises calculating a carbon content value using at least the first bulk property value and optionally the second bulk property value and/or non-hydrocarbon component concentration value in a carbon content correlation as discussed above. Computer 20 has a carbon content correlation 10 for calculating a carbon content value as a function of composition-dependent bulk properties and optionally concentration(s) of non-hydrocarbon component(s). Computer 20 calculates the carbon content value using the first composition-dependent bulk property value and optionally the second composition-dependent bulk property value and/or non-hydrocarbon component concentration value in carbon content correlation 10.

The method for producing the mixed feed further comprises selecting a desired steam-to-carbon ratio of the mixed feed. The desired steam-to-carbon ratio may be selected depending on the catalyst used, thermal efficiency considerations, and other operating parameters. The steam-to-carbon ratio is typically always on a molar basis but may be on a mass basis if desired.

The method for producing the mixed feed further comprises calculating a target flow rate of a steam-containing feed required to obtain the desired steam-to-carbon ratio of the mixed feed. This step of calculating uses the measured flow rate and the carbon content value as known in the art. Computer 20 may calculate the target flow rate of the steam-containing feed. The carbon content correlation may be explicit or imbedded in an equation for calculating the steam flow rate.

The method for producing the mixed feed further comprises regulating the steam-containing feed flow rate so that the steam-containing feed flow rate comes closer to or equal to the target flow rate. With reference to FIG. 8, computer 20 sends a signal to valve 80 and the flow rate of the steam-containing feed is regulated by valve 80. The resulting flow rate is a regulated flow rate.

The method for producing the mixed feed further comprises combining the hydrocarbon-containing mixture at the measured flow rate with the steam-containing feed at the regulated flow rate to form the mixed feed, shown in FIG. 8 as mixed feed 70.

Any of the various features described for the method for determining a carbon content value according to the first embodiment may be used in a method for producing a mixed feed for hydrogen production.

Figure 9:
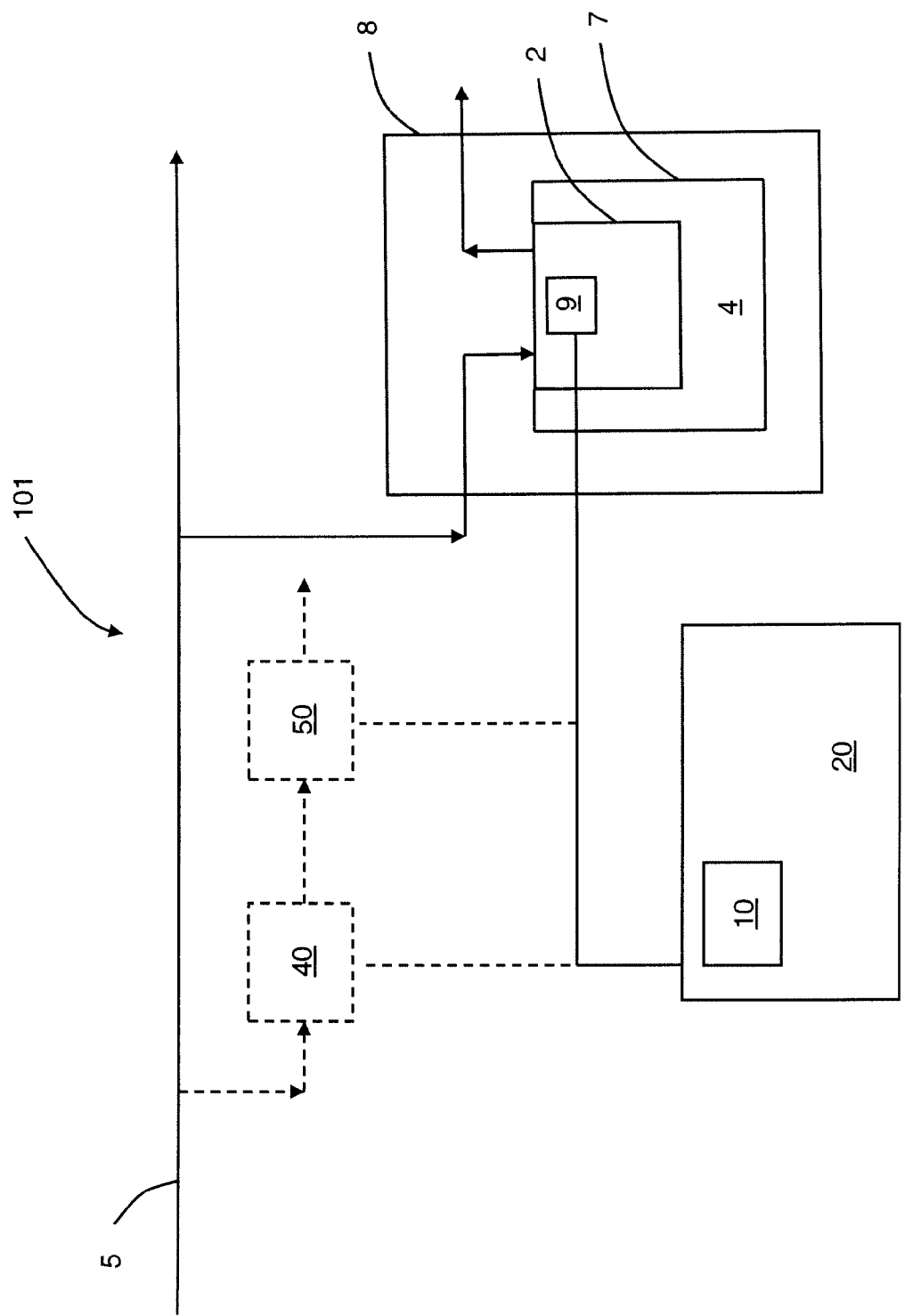
FIG. 9 is a schematic of an exemplary apparatus for performing a method for determining a carbon content value of a hydrocarbon-containing mixture.

Referring now to FIG. 9, which shows a schematic of an exemplary apparatus 101 for performing the method for determining a carbon content value of a hydrocarbon-containing mixture according to the second embodiment. Hydrocarbon-containing mixture 5 is introduced into vessel 2. Vessel 2 is in heat transfer and pressure regulating communication with a fixed mass of reference gas 4 in fixed-volume enclosure 7. Device 8 maintains the temperature and pressure of hydrocarbon-containing mixture 5 equal to the temperature and pressure of reference gas 4. Sensor 9 sends a signal to computer 20 and a density value is determined.

Hydrocarbon-containing mixture 5 is optionally sampled by optional sensor 40 for measuring a second composition-dependent bulk property. Optional sensor 40 may measure one of lower heating value, higher heating value, thermal conductivity, viscosity, molar heat capacity, specific heat capacity and sonic velocity. Sensor 40 sends a signal to computer 20 and a second composition-dependent bulk property value is determined.

Optionally, hydrocarbon-containing mixture 5 is sampled by optional sensor 50 for measuring a concentration of at least one non-hydrocarbon component in the hydrocarbon-containing mixture. In this instance, optional sensor 50 sends a signal to computer 20 and a non-hydrocarbon component concentration value is determined. Computer 20 has a carbon content correlation 10 for calculating a carbon content value as a function of composition-dependent bulk properties and/or non-hydrocarbon component concentrations. Computer 20 calculates the carbon content value using the density value and optionally the second composition-dependent bulk property value and optionally the non-hydrocarbon component concentration value in carbon content correlation 10. The carbon content value can then be used by the hydrogen production process to generate a desired steam-to-carbon ratio.

Device 8, optional sensor 40, and optional sensor 50 may be oriented in a variety of ways. Optional sensor 40 and optional sensor 50 may be mounted in the conduit containing the hydrocarbon-containing mixture. Alternatively, one or more slip streams may be taken from the conduit containing the hydrocarbon-containing mixture. Device 8, optional sensor 40 and optional sensor 50 may be mounted to measure the one or more slip streams. The slip stream may be conditioned, for example where the temperature and/or pressure are modified from the conditions of the process stream. In another alternative, one or more of sensor 40 and optional sensor 50 may be mounted in the conduit containing the hydrocarbon-containing mixture and the remaining sensor(s) mounted to measure a slip stream.

The second embodiment of the method for determining a carbon content value of a hydrocarbon-containing mixture including one or more of the various optional features may be used in a method for producing a mixed feed for hydrogen production.

Figure 10:
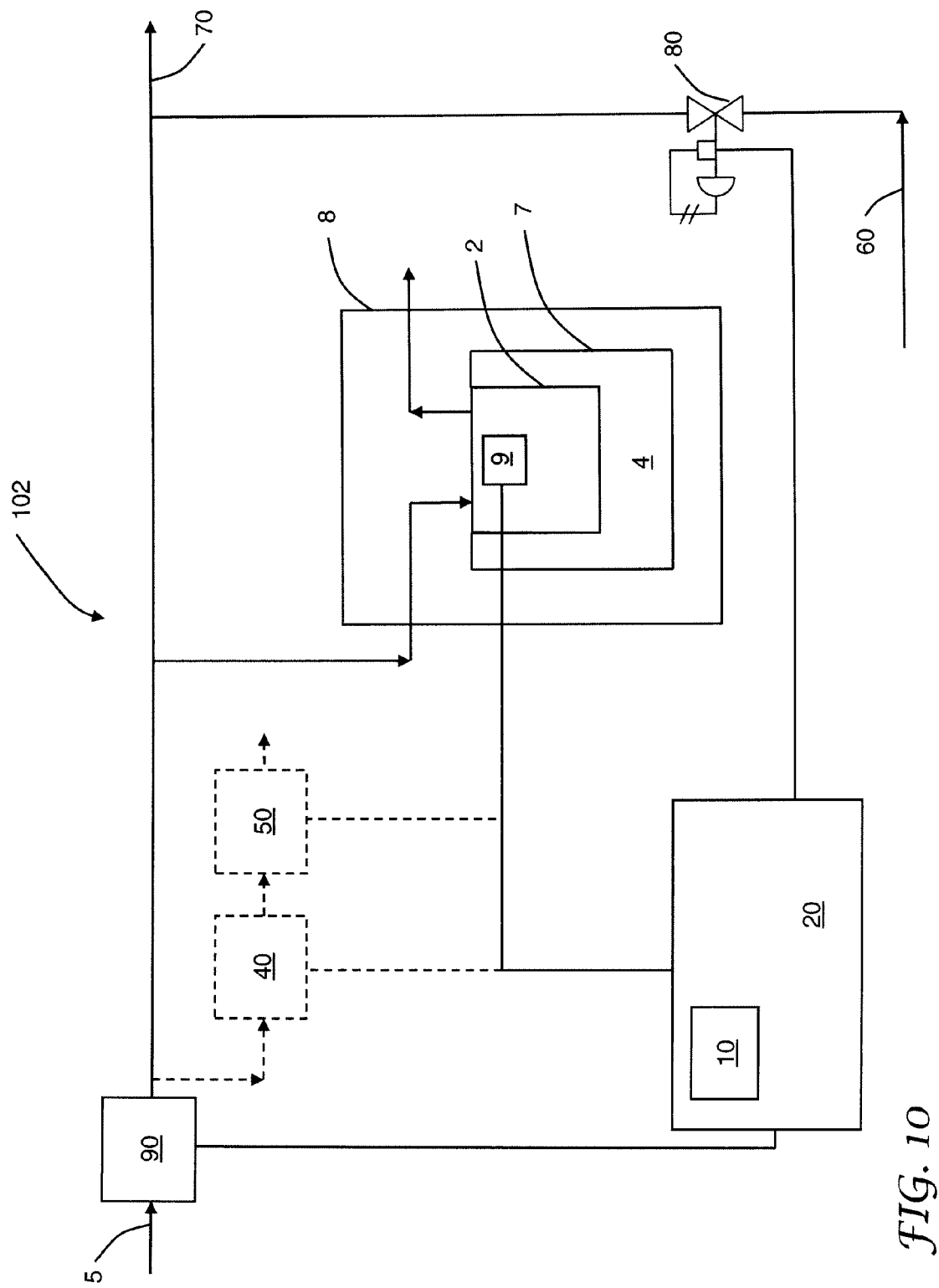
FIG. 10 is a schematic of an exemplary apparatus for performing a method for producing a mixed feed.

The method for producing a mixed feed for hydrogen or synthesis gas production using the second embodiment of the method for determining a carbon content value is described with reference to FIG. 10. FIG. 10 shows a schematic of an exemplary apparatus 102 for performing the method for producing a mixed feed.

The method for producing a mixed feed comprises measuring a flow rate of a hydrocarbon-containing mixture thereby obtaining a measured flow rate. As shown in FIG. 10, the flow rate of the hydrocarbon-containing mixture is measured by flowmeter 90 and flowmeter 90 sends a signal to computer 20 indicative of the flow rate. Suitable devices for measuring flow rate are known in the art.

The method for producing a mixed feed also comprises introducing the hydrocarbon-containing mixture 5 into vessel 2. Vessel 2 is in heat transfer and pressure regulating communication with a fixed mass of reference gas 4 in fixed-volume enclosure 7. Device 8 maintains the temperature and pressure of hydrocarbon-containing mixture 5 equal to the temperature and pressure of reference gas 4. Sensor 9 sends a signal computer 20 and a density value is determined.

Hydrocarbon-containing mixture 5 is optionally sampled by optional sensor 40 for measuring a first composition-dependent bulk property. Optional sensor 40 may measure one of lower heating value, higher heating value, thermal conductivity, viscosity, molar heat capacity, specific heat capacity and sonic velocity. Sensor 40 sends a signal to computer 20 and a first composition-dependent bulk property value is determined.

Optionally, hydrocarbon-containing mixture 5 is sampled by optional sensor 50 for measuring a concentration of at least one non-hydrocarbon component in the hydrocarbon-containing mixture. In this instance, optional sensor 50 sends a signal to computer 20 and a non-hydrocarbon component concentration value is determined. Computer 20 has a carbon content correlation 10 for calculating a carbon content value as a function of composition-dependent bulk properties and/or non-hydrocarbon component concentrations. Computer 20 calculates the carbon content value using the density value and optionally the first composition-dependent bulk property value and optionally the non-hydrocarbon component concentration value in carbon content correlation 10.

The method for producing the mixed feed further comprises calculating a carbon content value using at least the density value and optionally the second bulk property value and/or non-hydrocarbon component concentration value in a carbon content correlation as discussed above. Computer 20 has a carbon content correlation 10 for calculating a carbon content value as a function of composition-dependent bulk properties and optionally concentration(s) of non-hydrocarbon component(s). Computer 20 calculates the carbon content value using the density value and optionally the first composition-dependent bulk property value and/or non-hydrocarbon component concentration value in carbon content correlation 10.

The method for producing the mixed feed further comprises selecting a desired steam-to-carbon ratio of the mixed feed. The desired steam-to-carbon ratio may be selected depending on the catalyst used, thermal efficiency considerations, and other operating parameters. The steam-to-carbon ratio is typically always on a molar basis but may be on a mass basis if desired.

The method for producing the mixed feed further comprises calculating a target flow rate of a steam-containing feed required to obtain the desired steam-to-carbon ratio of the mixed feed. This step of calculating uses the measured flow rate and the carbon content value as known in the art. Computer 20 may calculate the target flow rate of the steam-containing feed. The carbon content correlation may be explicit or imbedded in an equation for calculating the steam flow rate.

The method for producing the mixed feed further comprises regulating the steam-containing feed flow rate so that the steam-containing feed flow rate comes closer to or equal to the target flow rate. With reference to FIG. 10, computer 20 sends a signal to valve 80 and the flow rate of the steam-containing feed is regulated by valve 80. The resulting flow rate is a regulated flow rate.

The method for producing the mixed feed further comprises combining the hydrocarbon-containing mixture at the measured flow rate with the steam-containing feed at the regulated flow rate to form the mixed feed, shown in FIG. 10 as mixed feed 70.

Any of the various features described for the method for determining a carbon content value according to the second embodiment may be used in the method for producing a mixed feed for hydrogen production.

EXAMPLES

The following examples compare the carbon numbers calculated from various correlations versus the actual carbon numbers for 11 samples of hydrocarbon-containing mixtures having known composition. The compositions of these 11 samples are given in Table 1 where the compositions have units of mole %. i-$C_4H_{10}$ is isobutane, i-$C_4H_8$ is isobutane, i-$C_5H_{12}$ is isopentane, and cis-2-$C_5H_{10}$ is cis-2-pentene. Various composition-dependent bulk properties are also given in Table 1 for samples 1 through 11.

Samples 1 through 10 are compositions corresponding to real samples taken from a hydrogen production facility. Some of the samples correspond to the hydrocarbon-containing mixture formed from natural gas. Other samples correspond to the hydrocarbon-containing mixture formed from a mixture of natural gas and butane. While other samples correspond to the hydrocarbon-containing mixture formed from natural gas, butane and refinery offgas.

All of the correlations generated for the examples used the data from samples 1 through 10.

Sample 11 is a hypothetical sample where sample 9 is modified by substituting 4 mole % of the methane with 4 mole % nitrogen. Sample 11 is used to illustrate the potential error when a hydrocarbon-containing mixture has a composition outside the range of the data used form the carbon content correlation.

The molecular weights shown in Table 1 were calculated from the molecular weight of the individual components and the concentration of that component.

The higher heating values, lower heating values molar heat capacities, specific heat capacities, viscosities, thermal conductivities and sonic velocities shown in Table 1 were calculated from physical property simulation software.

Example 1

Molecular Weight

In Example 1, a carbon content correlation is based on a single composition-dependent bulk property. The carbon content correlation was developed for carbon number as a function of molecular weight (MW).

Table 2 shows predicted versus actual carbon numbers for samples 1 through 11. The average relative error for samples 1 through 10 was about 2%.

The average relative error is the arithmetic average of the absolute values of the relative error of the carbon number. The relative error is the difference of the predicted carbon number and the actual carbon number, the difference divided by the actual carbon number.

The relative error for sample 11 is about 16%. While the average relative error for samples 1 through 10 is good, the error for sample 11 is not good. This illustrates the potential problem with a single composition-dependent bulk property correlation if the composition is outside the range used for developing the carbon content correlation. The error may be even larger if there are measurement inaccuracies solved by the method of the second embodiment.

Example 2

Molecular Weight and Higher Heating Value

In Example 2, a carbon content correlation is based on a two composition-dependent bulk properties. The carbon content correlation was developed for carbon number as a linear multivariable function of higher heating value (HHV) and molecular weight (MW).

Table 2 shows predicted versus actual carbon numbers for samples 1 through 11 for example 2. The average relative error for samples 1 through 10 is about 0.06%.

The relative error for sample 11 is about 0.07%. This example highlights that improved determination of carbon content may be obtained using at least two composition-dependent bulk properties, even when the composition of the hydrocarbon-containing mixture falls outside the range of data used for developing the carbon content correlation.

The extent of the improvement using two composition-dependent bulk properties in a multivariable function in the correlation was unexpected. The improvement for the average relative error for samples 1 through 10 is nearly an order of magnitude. The improvement for sample 11 was several orders of magnitude, 16% versus 0.07%.

A similar result can be expected for a method and/or correlation where the lower heating value is used in place of the higher heating value.

Example 3

Molecular Weight and Molar Heat Capacity

In Example 3, a carbon content correlation is based on a two composition-dependent bulk properties. The carbon content correlation was developed for carbon number as a linear multivariable function of molecular weight (MW) and molar heat capacity ($C_p$).

Table 2 shows predicted versus actual carbon numbers for samples 1 through 11. The average relative error for samples 1 through 10 was about 1.2%. The relative error for sample 11 is about 3%.

While not as good as the results in Example 2, this example shows an improvement over using the molecular weight alone as per Example 1.

Example 4

Molecular Weight and Thermal Conductivity

In Example 4, a carbon content correlation is based on a two composition-dependent bulk properties. The carbon content correlation was developed for carbon number as a linear multivariable function of molecular weight (MW) and thermal conductivity (k).

Table 2 shows predicted versus actual carbon numbers for samples 1 through 11. The average relative error for samples 1 through 10 was about 1.8%. The relative error for sample 11 is about 17%.

These results are on the order of the error using the molecular weight alone as per Example 1.

Example 5

Molecular Weight and Viscosity

In Example 5, a carbon content correlation is based on a two composition-dependent bulk properties. The carbon content correlation was developed for carbon number as a linear multivariable function of molecular weight (MW) and viscosity ($\mu$).

Table 2 shows predicted versus actual carbon numbers for samples 1 through 11. The average relative error for samples 1 through 10 was about 1.1%. The relative error for sample 11 is about 2.4%.

While not as good as the results in Example 2, this example shows an improvement over using the molecular weight alone as per Example 1.

Example 6

Molecular Weight and Sonic Velocity

In Example 6, a carbon content correlation is based on a two composition-dependent bulk properties. The carbon content correlation was developed for carbon number as a linear multivariable function of molecular weight (MW) and sonic velocity ($V_s$).

Table 2 shows predicted versus actual carbon numbers for samples 1 through 11. The average relative error for samples 1 through 10 was about 1.9%. The relative error for sample 11 is about 11.6%.

While not as good as the results in Example 2, this example shows a slight improvement over using the molecular weight alone as per Example 1.

Example 7

Molecular Weight and Specific Heat Capacity

In Example 7, a carbon content correlation is based on a two composition-dependent bulk properties. The carbon content correlation was developed for carbon number as a function of molecular weight (MW) and specific heat capacity ($c_p$).

Table 2 shows predicted versus actual carbon numbers for samples 1 through 11. The average relative error for samples 1 through 10 was about 1.2%. The relative error for sample 11 is about 3.8%.

While not as good as the results in Example 2, this example shows an improvement over using the molecular weight alone as per Example 1.

Example 8

Higher Heating Value and Molar Heat Capacity

In Example 8, a carbon content correlation is based on a two composition-dependent bulk properties. The carbon content correlation was developed for carbon number as a function of higher heating value (HHV) and molar heat capacity ($C_p$).

Table 2 shows predicted versus actual carbon numbers for samples 1 through 11. The average relative error for samples 1 through 10 was about 0.2%. The relative error for sample 11 is about 1.3%.

While not as good as the results in Example 2, this example shows a marked improvement over using the molecular weight alone as per Example 1.

Example 9

Higher Heating Value and Thermal Conductivity

In Example 9, a carbon content correlation is based on a two composition-dependent bulk properties. The carbon content correlation was developed for carbon number as a function of higher heating value (HHV) and thermal conductivity (k).

Table 2 shows predicted versus actual carbon numbers for samples 1 through 11. The average relative error for samples 1 through 10 was about 0.2%. The relative error for sample 11 is about 1.9%.

While not as good as the results in Example 2, this example shows a marked improvement over using the molecular weight alone as per Example 1.

A similar result can be expected for a method and/or correlation where the lower heating value is used in place of the higher heating value.

Example 10

Higher Heating Value and Viscosity

In Example 10, a carbon content correlation is based on a two composition-dependent bulk properties. The carbon content correlation was developed for carbon number as a function of higher heating value (HHV) and viscosity ($\mu$).

Table 2 shows predicted versus actual carbon numbers for samples 1 through 11. The average relative error for samples 1 through 10 was about 0.3%. The relative error for sample 11 is about 1.6%.

While not as good as the results in Example 2, this example shows a marked improvement over using the molecular weight alone as per Example 1.

A similar result can be expected for a method and/or correlation where the lower heating value is used in place of the higher heating value.

Example 11

Higher Heating Value and Sonic Velocity

In Example 11, a carbon content correlation is based on a two composition-dependent bulk properties. The carbon content correlation was developed for carbon number as a function of higher heating value (HHV) and sonic velocity ($V_s$).

Table 2 shows predicted versus actual carbon numbers for samples 1 through 11. The average relative error for samples 1 through 10 was about 0.1%. The relative error for sample 11 is about 0.3%.

These results are nearly as good as the results in Example 2. This example shows a marked improvement over using the molecular weight alone as per Example 1.

A similar result can be expected for a method and/or correlation where the lower heating value is used in place of the higher heating value.

Example 12

Higher Heating Value and Specific Heat Capacity

In Example 12, a carbon content correlation is based on a two composition-dependent bulk properties. The carbon content correlation was developed for carbon number as a function of higher heating value (HHV) and specific heat capacity ($c_p$).

Table 2 shows predicted versus actual carbon numbers for samples 1 through 11. The average relative error for samples 1 through 10 was about 0.1%. The relative error for sample 11 is about 0.5%.

Results for higher heating value and specific heat capacity are comparable to the results in Example 2. This example shows a marked improvement over using the molecular weight alone as per Example 1.

A similar result can be expected for a method and/or correlation where the lower heating value is used in place of the higher heating value.

Example 13

Thermal Conductivity and Molar Heat Capacity

In Example 13, a carbon content correlation is based on a two composition-dependent bulk properties. The carbon content correlation was developed for carbon number as a function of thermal conductivity and molar heat capacity ($C_p$).

Table 2 shows predicted versus actual carbon numbers for samples 1 through 11. The average relative error for samples 1 through 10 was about 0.5%. The relative error for sample 11 is about 5%.

While not as good as the results in Example 2, this example shows a marked improvement over using the molecular weight alone as per Example 1.

Example 14

Thermal Conductivity and Viscosity

In Example 14, a carbon content correlation is based on a two composition-dependent bulk properties. The carbon content correlation was developed for carbon number as a function of thermal conductivity and viscosity (μ).

Table 2 shows predicted versus actual carbon numbers for samples 1 through 11. The average relative error for samples 1 through 10 was about 1%. The relative error for sample 11 is about 8%.

While not as good as the results in Example 2, this example shows an improvement over using the molecular weight alone as per Example 1

Example 15

Thermal Conductivity and Sonic Velocity

In Example 15, a carbon content correlation is based on a two composition-dependent bulk properties. The carbon content correlation was developed for carbon number as a linear multivariable function of thermal conductivity and sonic velocity ($V_s$).

Table 2 shows predicted versus actual carbon numbers for samples 1 through 11. The average relative error for samples 1 through 10 was about 1.5%. The relative error for sample 11 is about 15%.

These results are on the order of the error using the molecular weight alone as per Example 1.

Example 16

Thermal Conductivity and Specific Heat Capacity

In Example 16, a carbon content correlation is based on a two composition-dependent bulk properties. The carbon content correlation was developed for carbon number as a linear multivariable function of thermal conductivity and specific heat capacity ($c_p$).

Table 2 shows predicted versus actual carbon numbers for samples 1 through 11. The average relative error for samples 1 through 10 was about 6%. The relative error for sample 11 is about 17%.

The error using these composition-dependent bulk properties is worse than the error using the molecular weight alone as per Example 1.

Example 17

Sonic Velocity and Molar Heat Capacity

In Example 17, a carbon content correlation is based on a two composition-dependent bulk properties. The carbon content correlation was developed for carbon number as a linear multivariable function of sonic velocity ($V_s$) and molar heat capacity ($C_p$).

Table 2 shows predicted versus actual carbon numbers for samples 1 through 11. The average relative error for samples 1 through 10 was about 1%. The relative error for sample 11 is about 2%.

While not as good as the results in Example 2, this example shows a marked improvement over using the molecular weight alone as per Example 1.

Example 18

Sonic Velocity and Viscosity

In Example 18, a carbon content correlation is based on a two composition-dependent bulk properties. The carbon content correlation was developed for carbon number as a linear multivariable function of sonic velocity ($V_s$) and viscosity (μ).

Table 2 shows predicted versus actual carbon numbers for samples 1 through 11. The average relative error for samples 1 through 10 was about 1%. The relative error for sample 11 is about 2%.

While not as good as the results in Example 2, this example shows a marked improvement over using the molecular weight alone as per Example 1.

Example 19

Sonic Velocity and Specific Heat Capacity

In Example 19, a carbon content correlation is based on a two composition-dependent bulk properties. The carbon content correlation was developed for carbon number as a linear multivariable function of sonic velocity ($V_s$) and specific heat capacity ($c_p$).

Table 2 shows predicted versus actual carbon numbers for samples 1 through 11. The average relative error for samples 1 through 10 was about 1%. The relative error for sample 11 is about 4%.

While not as good as the results in Example 2, this example shows a marked improvement over using the molecular weight alone as per Example 1.

Example 20

Higher Heating Value, Molar Heat Capacity and Molecular Weight

In Example 20, a carbon content correlation is based on a three composition-dependent bulk properties. The carbon content correlation was developed for carbon number as a linear multivariable function of higher heating value (HHV) and molar heat capacity ($C_p$) and molecular weight (MW).

Table 2 shows predicted versus actual carbon numbers for samples 1 through 11 for example 20. The average relative error for samples 1 through 10 was about 0.04%. The relative error for sample 11 is about 0.08%.

Results for higher heating value, molar heat capacity and molecular weight are about the same as the results in Example 2. This example shows a marked improvement over using the molecular weight alone as per Example 1.

A similar result can be expected for a method and/or correlation where the lower heating value is used in place of the higher heating value.

Example 21

Higher Heating Value, Thermal Conductivity and Molecular Weight

In Example 21, a carbon content correlation is based on a linear function of three composition-dependent bulk properties. The carbon content correlation was developed for carbon number as a linear multivariable function of higher heating value (HHV), thermal conductivity (k) and molecular weight (MW).

Table 2 shows predicted versus actual carbon numbers for samples 1 through 11 for example 21. The average relative error for samples 1 through 10 was about 0.04%. The relative error for sample 11 is about 0.07%.

Results for higher heating value, thermal conductivity and molecular weight are slightly better than the results in Example 2. This example shows a marked improvement over using the molecular weight alone as per Example 1.

A similar result can be expected for a method and/or correlation where the lower heating value is used in place of the higher heating value.

Example 22

Higher Heating Value and Molecular Weight

In Example 22, a carbon content correlation is based on a nonlinear function of two composition-dependent bulk properties. The function includes cross-multiplied and second order terms. The carbon content correlation was developed for carbon number as a function of higher heating value (HHV) and molecular weight (MW).

Table 2 shows predicted versus actual carbon numbers for samples 1 through 11. The average relative error for samples 1 through 10 was about 0.01%.

The relative error for sample 11 is about 1%.

This example illustrates that nonlinear functions may also be used which also provide good results.

A similar result can be expected for a method and/or correlation where the lower heating value is used in place of the higher heating value.

Example 23

Higher Heating Value

In Example 23, a carbon content correlation is based on a single composition-dependent bulk proper, higher heating value.

Table 2 shows predicted versus actual carbon numbers for samples 1 through 11 for example 23. The average relative error for samples 1 through 10 was about 0.45%. The relative error for sample 11 is about 2.12%.

This example shows a marked improvement over using the molecular weight alone as per Example 1.

Example 24

Higher Heating Value and Nitrogen Concentration

In Example 24, a carbon content correlation based on Equation 9 and based on a function of higher heating value and nitrogen concentration. Hydrogen and carbon monoxide are grouped with the hydrocarbons. In this case, since the concentration of carbon dioxide is small, carbon dioxide is also grouped with the hydrocarbons for this correlation. The only outlier component considered is nitrogen.

Table 2 shows the predicted versus actual carbon numbers for samples 1 through 11 for Example 24. The average relative error for samples 1 through 10 was about 0.14%. The relative error for sample 11 is about 0.12%.

This example shows the improvement provided by including a correction for nitrogen concentration.

Example 25

Molecular Weight and Nitrogen Concentration

In Example 25, a carbon content correlation based on Equation 9 and based on a function of molecular weight and nitrogen concentration. Hydrogen, carbon monoxide and carbon dioxide are grouped with the hydrocarbons. The only outlier component considered is nitrogen.

Table 2 shows the predicted versus actual carbon numbers for samples 1 through 11 for Example 25. The average relative error for samples 1 through 10 was about 0.38%. The relative error for sample 11 is about 0.56%.

This example shows the improvement provided by including a correction for nitrogen concentration.

TABLE 1

| | Sample 1 | Sample 2 | Sample 3 | Sample 4 | Sample 5 | Sample 6 |
|---|---|---|---|---|---|---|
| Component | | | | | | |
| $N_2$ | 1.050 | 1.020 | 0.788 | 0.795 | 1.520 | 1.360 |
| $CO_2$ | 0.290 | 0.310 | 0.960 | 0.477 | 0.380 | 0.760 |
| $CO$ | 0.360 | 0.370 | 0.000 | 0.298 | 0.210 | 0.000 |
| $H_2$ | 10.896 | 10.197 | 0.000 | 7.659 | 4.780 | 0.000 |
| $CH_4$ | 75.773 | 74.780 | 95.774 | 80.465 | 85.631 | 95.089 |
| $C_2H_4$ | 0.000 | 0.000 | 0.000 | 0.000 | 0.000 | 0.000 |
| $C_2H_6$ | 2.109 | 2.099 | 2.275 | 1.907 | 1.590 | 2.380 |
| $C_3H_6$ | 0.000 | 0.000 | 0.000 | 0.010 | 0.000 | 0.000 |
| $C_3H_8$ | 0.250 | 0.260 | 0.153 | 0.248 | 0.180 | 0.290 |
| $i\text{-}C_4H_{10}$ | 0.530 | 0.580 | 0.019 | 0.199 | 0.056 | 0.034 |
| $C_4H_{10}$ | 8.677 | 10.297 | 0.021 | 7.172 | 5.469 | 0.048 |
| $i\text{-}C_4H_8$ | 0.000 | 0.000 | 0.000 | 0.000 | 0.000 | 0.000 |
| $i\text{-}C_5H_{12}$ | 0.026 | 0.035 | 0.006 | 0.526 | 0.140 | 0.011 |
| $C_5H_{12}$ | 0.010 | 0.014 | 0.004 | 0.219 | 0.019 | 0.010 |
| $cis\text{-}2\text{-}C_5H_{10}$ | 0.000 | 0.000 | 0.000 | 0.000 | 0.000 | 0.000 |
| $C_6H_{14}$ | 0.029 | 0.038 | 0 | 0.025 | 0.025 | 0.019 |
| Property | | | | | | |
| $N_c$ (mol C/mol) | 1.18 | 1.24 | 1.01 | 1.18 | 1.12 | 1.01 |
| MW (g/gmol) | 19.05 | 19.86 | 16.79 | 19.11 | 18.39 | 16.89 |
| HHV (kJ/gmol) | 1014 | 1052 | 894 | 1015 | 972 | 895 |
| LHV (kJ/gmol) | 918 | 953 | 806 | 919 | 879 | 806 |
| $C_p$ (kJ/kg K) | 2.786 | 2.760 | 2.735 | 2.758 | 2.739 | 2.726 |
| $C_p$ (kJ/kgmol K) | 53.05 | 54.82 | 45.93 | 52.70 | 50.37 | 46.04 |
| k (W/m K) | 0.0687 | 0.0671 | 0.0611 | 0.0657 | 0.0638 | 0.0610 |
| $\mu$ (N/m$^2$ s) | 1.63E−05 | 1.62E−05 | 1.69E−05 | 1.63E−05 | 1.65E−05 | 1.69E−05 |
| $V_s$ (m/s) | 498 | 486 | 538 | 497 | 509 | 536 |

TABLE 1-continued

|  | Sample 7 | Sample 8 | Sample 9 | Sample 10 | Sample 11 |
|---|---|---|---|---|---|
| Component |  |  |  |  |  |
| $N_2$ | 2.103 | 2.920 | 6.000 | 4.512 | 10 |
| $CO_2$ | 0.573 | 0.586 | 0.756 | 0.230 | 0.76 |
| CO | 0.000 | 0.000 | 0.000 | 0.500 | 0 |
| $H_2$ | 0.000 | 0.000 | 0.000 | 19.408 | 0 |
| $CH_4$ | 94.777 | 94.282 | 90.802 | 55.922 | 86.8 |
| $C_2H_4$ | 0.000 | 0.000 | 0.000 | 4.602 | 0 |
| $C_2H_6$ | 2.204 | 1.888 | 2.183 | 9.324 | 2.18 |
| $C_3H_6$ | 0.000 | 0.000 | 0.000 | 1.371 | 0 |
| $C_3H_8$ | 0.226 | 0.228 | 0.178 | 3.021 | 0.18 |
| $i\text{-}C_4H_{10}$ | 0.034 | 0.038 | 0.027 | 0.090 | 0.03 |
| $C_4H_{10}$ | 0.039 | 0.041 | 0.025 | 0.190 | 0.02 |
| $i\text{-}C_4H_8$ | 0.000 | 0.000 | 0.000 | 0.100 | 0 |
| $i\text{-}C_5H_{12}$ | 0.012 | 0.000 | 0.000 | 0.170 | 0 |
| $C_5H_{12}$ | 0.009 | 0.000 | 0.000 | 0.150 | 0 |
| $cis\text{-}2\text{-}C_5H_{10}$ | 0.000 | 0.000 | 0.000 | 0.090 | 0 |
| $C_6H_{14}$ | 0.023 | 0.017 | 0.030 | 0.320 | 0.03 |
| Property |  |  |  |  |  |
| $N_c$ (mol C/mol) | 1.00 | 0.99 | 0.96 | 1.02 | 0.92 |
| MW (g/gmol) | 16.89 | 16.93 | 17.37 | 17.66 | 17.85 |
| HHV (kJ/gmol) | 888 | 878 | 850 | 900 | 814 |
| LHV (kJ/gmol) | 800 | 791 | 766 | 815 | 734 |
| $C_p$ (kJ/kg K) | 2.714 | 2.692 | 2.599 | 2.760 | 2.494 |
| $C_p$ (kJ/kgmol K) | 45.83 | 45.58 | 45.15 | 48.75 | 44.51 |
| k (W/m K) | 0.0609 | 0.0608 | 0.0599 | 0.0770 | 0.0589 |
| μ (N/m² s) | 1.69E-05 | 1.7E-05 | 1.72E-05 | 1.66E-05 | 1.74E-05 |
| $V_s$ (m/s) | 537 | 537 | 530 | 522 | 524 |

TABLE 2

| Sample | $N_c$ Actual | Example 1 | Example 2 | Example 3 | Example 4 | Example 5 | Example 6 |
|---|---|---|---|---|---|---|---|
| 1 | 1.18 | 1.17 | 1.18 | 1.19 | 1.17 | 1.18 | 1.18 |
| 2 | 1.24 | 1.24 | 1.24 | 1.23 | 1.24 | 1.23 | 1.22 |
| 3 | 1.01 | 0.98 | 1.01 | 1.00 | 0.98 | 1.00 | 0.98 |
| 4 | 1.18 | 1.17 | 1.18 | 1.18 | 1.18 | 1.18 | 1.18 |
| 5 | 1.12 | 1.11 | 1.12 | 1.11 | 1.12 | 1.12 | 1.13 |
| 6 | 0.96 | 1.03 | 0.96 | 0.97 | 1.03 | 0.97 | 1.01 |
| 7 | 1.01 | 0.99 | 1.01 | 1.00 | 0.99 | 1.00 | 0.99 |
| 8 | 1.00 | 0.99 | 1.00 | 0.99 | 0.99 | 1.00 | 0.99 |
| 9 | 0.99 | 0.99 | 0.99 | 0.99 | 0.99 | 0.99 | 0.99 |
| 10 | 1.02 | 1.05 | 1.03 | 1.07 | 1.04 | 1.07 | 1.07 |
| 11 | 0.92 | 1.07 | 0.92 | 0.95 | 1.08 | 0.94 | 1.03 |

| Sample | Example 7 | Example 8 | Example 9 | Example 10 | Example 11 | Example 12 | Example 13 |
|---|---|---|---|---|---|---|---|
| 1 | 1.18 | 1.18 | 1.18 | 1.18 | 1.18 | 1.18 | 1.18 |
| 2 | 1.23 | 1.23 | 1.23 | 1.23 | 1.24 | 1.24 | 1.24 |
| 3 | 1.00 | 1.01 | 1.01 | 1.01 | 1.01 | 1.01 | 1.00 |
| 4 | 1.18 | 1.18 | 1.18 | 1.18 | 1.18 | 1.18 | 1.18 |
| 5 | 1.11 | 1.12 | 1.12 | 1.12 | 1.12 | 1.12 | 1.12 |
| 6 | 0.97 | 0.96 | 0.95 | 0.95 | 0.96 | 0.96 | 0.98 |
| 7 | 1.00 | 1.01 | 1.02 | 1.02 | 1.01 | 1.01 | 1.00 |
| 8 | 0.99 | 1.00 | 1.01 | 1.01 | 1.00 | 1.01 | 1.00 |
| 9 | 0.99 | 0.99 | 0.99 | 0.99 | 0.99 | 0.99 | 0.99 |
| 10 | 1.07 | 1.03 | 1.02 | 1.02 | 1.03 | 1.02 | 1.02 |
| 11 | 0.96 | 0.91 | 0.90 | 0.91 | 0.92 | 0.92 | 0.97 |

| Sample | Example 14 | Example 15 | Example 16 | Example 17 | Example 18 | Example 19 | Example 20 |
|---|---|---|---|---|---|---|---|
| 1 | 1.18 | 1.17 | 1.15 | 1.19 | 1.18 | 1.19 | 1.18 |
| 2 | 1.23 | 1.23 | 1.11 | 1.23 | 1.23 | 1.22 | 1.24 |
| 3 | 1.03 | 0.98 | 1.09 | 1.00 | 1.00 | 1.00 | 1.01 |
| 4 | 1.18 | 1.18 | 1.11 | 1.17 | 1.18 | 1.18 | 1.18 |
| 5 | 1.12 | 1.12 | 1.09 | 1.11 | 1.12 | 1.12 | 1.12 |
| 6 | 0.93 | 1.03 | 0.91 | 0.97 | 0.97 | 0.97 | 0.96 |
| 7 | 1.03 | 0.99 | 1.07 | 1.00 | 1.00 | 1.00 | 1.01 |

TABLE 2-continued

| | | | | | | | |
|---|---|---|---|---|---|---|---|
| 8 | 1.01 | 0.99 | 1.06 | 1.00 | 1.00 | 0.99 | 1.00 |
| 9 | 0.99 | 0.99 | 1.03 | 0.99 | 0.99 | 0.99 | 0.99 |
| 10 | 1.03 | 1.04 | 1.11 | 1.07 | 1.07 | 1.08 | 1.02 |
| 11 | 0.85 | 1.06 | 0.77 | 0.94 | 0.94 | 0.96 | 0.92 |

| Sample | Example 21 | Example 22 | Example 23 | Example 24 | Example 25 |
|---|---|---|---|---|---|
| 1 | 1.18 | 1.18 | 1.19 | 1.18 | 1.18 |
| 2 | 1.24 | 1.24 | 1.24 | 1.23 | 1.24 |
| 3 | 1.01 | 1.01 | 1.02 | 1.01 | 1.02 |
| 4 | 1.18 | 1.18 | 1.19 | 1.18 | 1.19 |
| 5 | 1.12 | 1.12 | 1.13 | 1.12 | 1.12 |
| 6 | 0.96 | 1.01 | 1.02 | 1.01 | 1.02 |
| 7 | 1.01 | 1.00 | 1.01 | 1.00 | 1.00 |
| 8 | 1.00 | 0.99 | 0.99 | 0.99 | 0.99 |
| 9 | 0.99 | 0.96 | 0.95 | 0.96 | 0.97 |
| 10 | 1.02 | 1.02 | 1.02 | 1.03 | 1.01 |
| 11 | 0.92 | 0.93 | 0.90 | 0.92 | 0.93 |

We claim:

1. A method for determining a carbon content value of a hydrocarbon-containing mixture comprising:

measuring a first composition-dependent bulk property of the hydrocarbon-containing mixture using a first sensor to determine a first composition-dependent bulk property value, the first composition-dependent bulk property selected from the group consisting of lower heating value, higher heating value, thermal conductivity, viscosity, molar heat capacity, specific heat capacity, and sonic velocity;

measuring a concentration of at least one non-hydrocarbon component in the hydrocarbon-containing mixture using a second sensor to determine a non-hydrocarbon component concentration value and/or measuring a second composition-dependent bulk property of the hydrocarbon-containing mixture using a third sensor to determine a second composition-dependent bulk property value, the at least one non-hydrocarbon component selected from the croup consisting of nitrogen, carbon monoxide, and carbon dioxide; and calculating the carbon content value using the first composition-dependent bulk property value and using the non-hydrocarbon component concentration value and/or the second composition-dependent bulk property value in a carbon content correlation.

2. The method of claim 1 wherein the method comprises:

measuring the concentration of the at least one non-hydrocarbon component in the hydrocarbon-containing mixture using the second sensor to determine the non-hydrocarbon component concentration value; and calculating the carbon content value using the first composition-dependent bulk property value and using the non-hydrocarbon component concentration value in the carbon content correlation.

3. The method of claim 1 wherein the method comprises:

measuring the second composition-dependent bulk property of the hydrocarbon-containing mixture using the third sensor to determine the second composition-dependent bulk property value; and calculating the carbon content value using the first composition-dependent bulk property value and using the second composition-dependent bulk property value in the carbon content correlation.

4. The method of claim 3 wherein the carbon content correlation is a multivariable function of the first composition-dependent bulk property and the second composition-dependent bulk property.

5. The method of claim 3 wherein the second composition-dependent bulk property is selected from the group consisting of lower heating value, higher heating value, thermal conductivity, viscosity, molecular weight, density, molar heat capacity, specific heat capacity, and sonic velocity.

6. The method of claim 3 wherein the first composition-dependent bulk property is higher heating value or lower heating value and the second composition-dependent bulk property is one of molecular weight, molar heat capacity, thermal conductivity, viscosity or sonic velocity.

7. The method of claim 3 wherein the first composition-dependent bulk property is viscosity and the second composition-dependent bulk property is molecular weight or sonic velocity.

8. A method for determining a carbon content value of a hydrocarbon-containing mixture comprising:

measuring a first composition-dependent bulk property of the hydrocarbon-containing mixture using a sensor to determine a first composition-dependent bulk property value, the first composition-dependent bulk property selected from the group consisting of lower heating value, higher heating value, thermal conductivity, viscosity, molar heat capacity, specific heat capacity, and sonic velocity;

measuring a second composition-dependent bulk property of the hydrocarbon-containing mixture using another sensor to determine a second composition-dependent bulk property value;

measuring a third composition-dependent bulk property of the hydrocarbon-containing mixture to determine a third composition-dependent bulk property value, and calculating the carbon content value using the first composition-dependent bulk property value, using the second composition-dependent bulk property value, and using the third composition-dependent bulk property value in a carbon content correlation.

9. A method for producing a mixed feed for hydrogen or synthesis gas production comprising:

measuring a first flow rate of a hydrocarbon-containing mixture thereby obtaining a measured flow rate value;

the method of claim 1 for determining a carbon content value of the hydrocarbon-containing mixture;

selecting a desired steam-to-carbon ratio of the mixed feed;
calculating a target flow rate of a steam-containing feed required to obtain the desired steam-to-carbon ratio of the mixed feed using the measured flow rate value and the carbon content value, the steam-containing feed having a steam-containing feed flow rate;
regulating the steam-containing feed flow rate so that the steam-containing feed flow rate comes closer to or equal to the target flow rate, thereby obtaining a regulated flow rate; and
combining the hydrocarbon-containing mixture at the first flow rate with the steam-containing feed at the regulated flow rate to form the mixed feed.

10. The method of claim 9 wherein the method comprises:
measuring the concentration of the at least one non-hydrocarbon component in the hydrocarbon-containing mixture using the second sensor to determine the non-hydrocarbon component concentration value; and
calculating the carbon content value using the first composition-dependent bulk property value and using the non-hydrocarbon component concentration value in the carbon content correlation.

11. The method of claim 9 wherein the method comprises:
measuring the second composition-dependent bulk property of the hydrocarbon-containing mixture using the third sensor to determine the second composition-dependent bulk property value; and
calculating the carbon content value using the first composition-dependent bulk property value and using the second composition-dependent bulk property value in the carbon content correlation.

* * * * *

UNITED STATES PATENT AND TRADEMARK OFFICE
CERTIFICATE OF CORRECTION

Page 1 of 1

PATENT NO.        : 7,871,826 B2
APPLICATION NO.   : 11/861651
DATED             : January 18, 2011
INVENTOR(S)       : Peng et al.

It is certified that error appears in the above-identified patent and that said Letters Patent is hereby corrected as shown below:

Column 33

Line 41, delete "croup" and insert -- group --

Signed and Sealed this
Twenty-first Day of June, 2011

David J. Kappos
*Director of the United States Patent and Trademark Office*